United States Patent [19]

Chikaraishi

[11] Patent Number: 5,591,626
[45] Date of Patent: Jan. 7, 1997

[54] EXPRESSION OF A TARGET GENE IN TRANSGENIC MAMMALS WITH 5' FLANKING SEQUENCES OF THE RAT TYROSINE HYDROXYLASE GENE

[75] Inventor: Dona M. Chikaraishi, Boston, Mass.

[73] Assignee: Trustees of Tufts College, Medford, Mass.

[21] Appl. No.: 292,926

[22] Filed: Aug. 18, 1994

Related U.S. Application Data

[63] Continuation of Ser. No. 973,032, Nov. 6, 1992, abandoned.
[51] Int. Cl.$^6$ .................................................... C12N 5/00
[52] U.S. Cl. ............................ 435/240.2; 435/240.1; 536/23.1; 536/23.72; 536/24.1; 800/2; 800/DIG. 1; 935/6; 935/70
[58] Field of Search .............................. 435/240.1, 240.2; 800/2, DIG. 1; 536/24.1, 23.1, 23.72; 935/6, 70

[56] References Cited

PUBLICATIONS

R. M. Fedderson (1992) Neuron 9:955–966.
P. L. Mellon et al (1990) Neuron 6:1–10.
F. Cambi et al (1989) J. Neurochemistry 63:1656–1659.
Adams and Corey, Science, 253:1161–1167, 1991.
Baetge et al., Proc. Natl. Acad. Sci., USA, 85:3648–3652, 1988.
Banerjee and Chikaraishi, Soc. Neurosci. Abstr., 17:530, 1991.
Cambi et al., J. Neurochem., 53:1656–1659, 1989.
Fung et al., J. Neurochem., 58:2044–2052, 1992.
Hammang et al., Neuron, 4:775–782, 1990.
Jat et al., Proc. Natl. Acad. Sci. USA, 88:5096–5100, 1991.
Joh et al., Abstr. Soc. Neurosci., 18;239, 1992.
Kaneda et al., Neuron, 6:583–594, 1991.
Lewis et al., Proc. Natl. Acad. Sci. USA, 84:3550–3554, 1987.
Maxwell et al., Mol. Cell. Biol., 7:1576–1579, 1987.
Mellon et al., Neuron, 5:1–10, 1990.
Morgan and Sharp, Abstr. Soc. Neurosci., 17, 1991.
Selden et al., Mol. Cell. Biol., 6:3173–3179, 1986.
Suri, Fung, Chikaraishi, Soc. Neurosci. Abstr. 17:528, 1991.
Yoon and Chikaraishi, Neuron, 9:55–67, 1992.

*Primary Examiner*—Jasemine C. Chambers
*Assistant Examiner*—Bruce R. Campell
*Attorney, Agent, or Firm*—David G. Conlin; Peter F. Corless; David S. Resnick

[57] ABSTRACT

Expession of a target gene or transene in catecholaminergic cells of a transgenic mammal operably linked to the 5' flanlking sequence of a rat tyrosine hydroxylase gene is disclosed as well as immortalized catecholaminergic neuronal cell lines employing an oncogene operably linked to the 5' flanking sequence of a rat tyrosine hydroxylase gene.

2 Claims, 17 Drawing Sheets

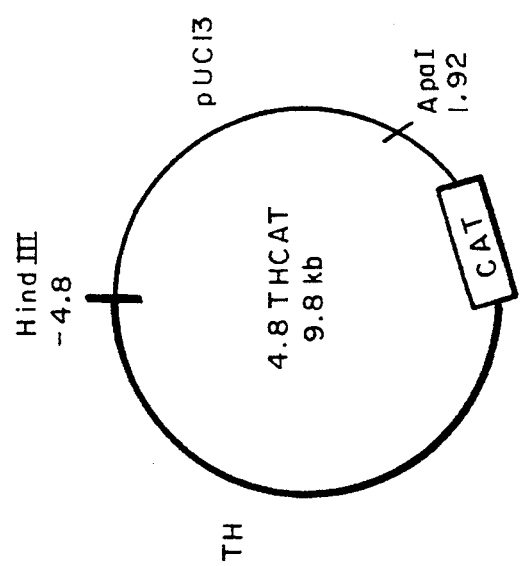
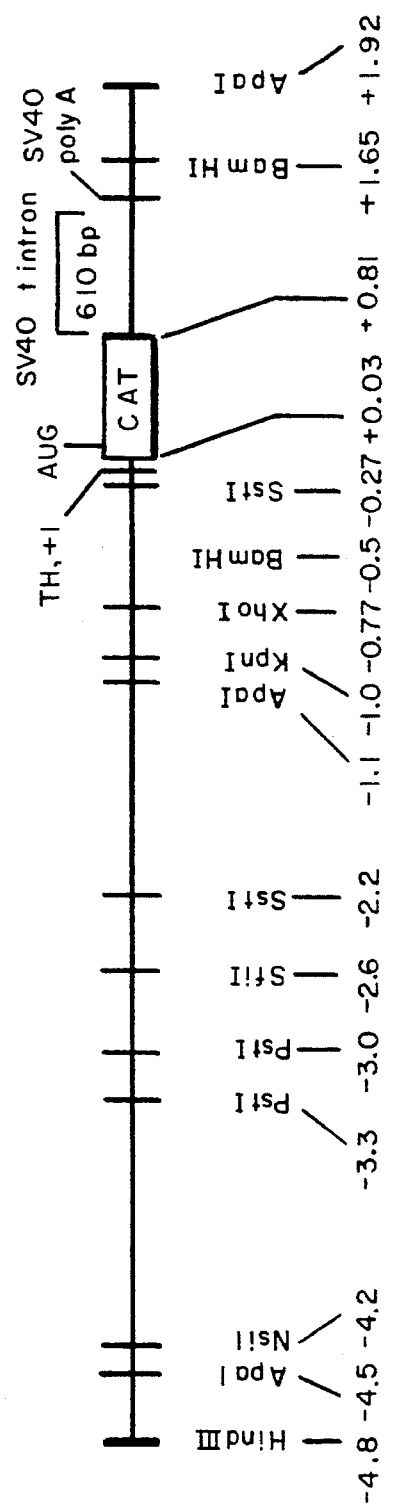
FIG. 1

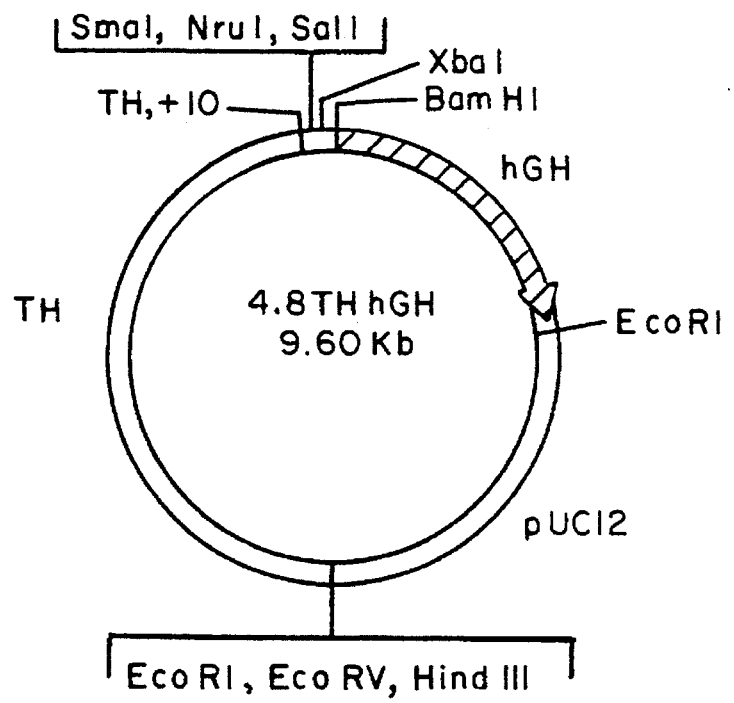
- ▨ EXONS
- ▢ Introns
- ▧ 3' flanking region
The hGH gene
(Selden et al, Mol. Cell. Biol. 6, 3173-3179, 1986)
FIG. 4B

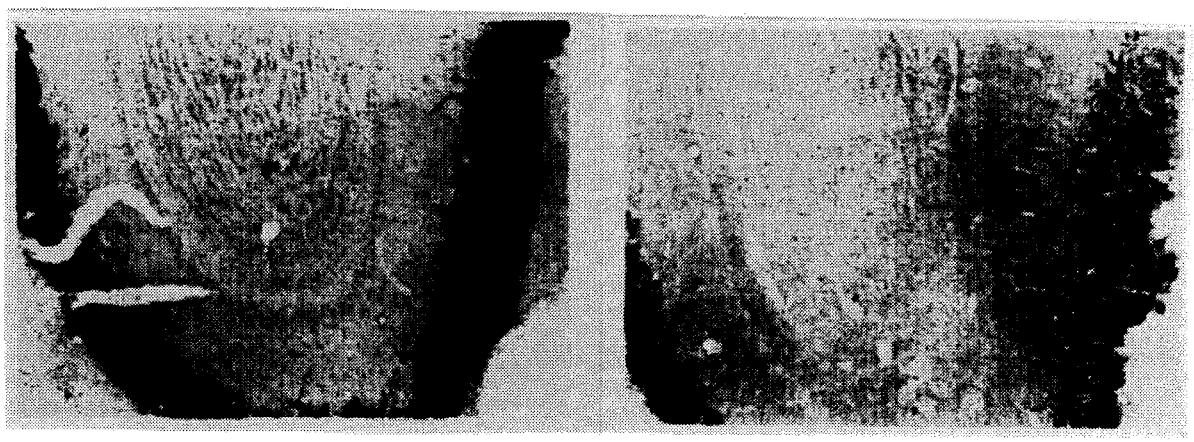
FIG.IIAa  FIG.IIAb
FIG.IIBa  FIG.IIBb
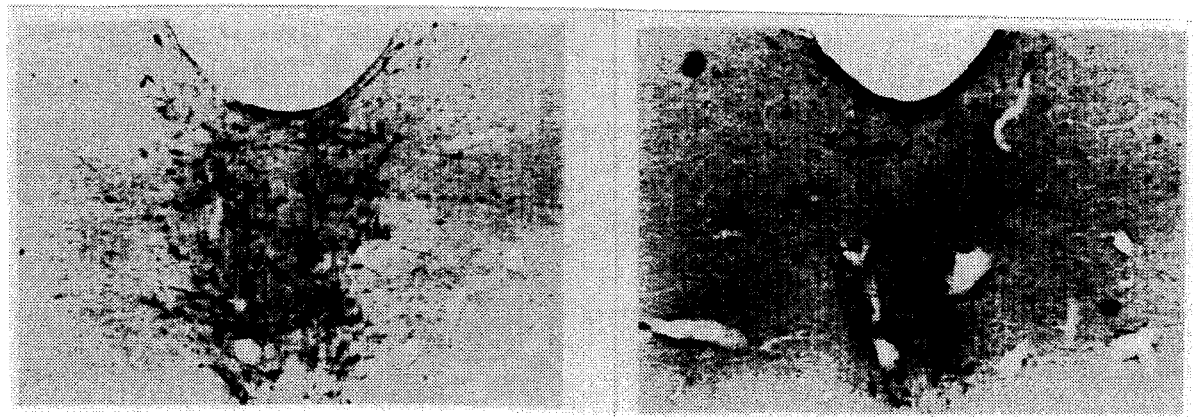
FIG.IICa  FIG.IICb

FIG.IIDa
FIG.IIDb
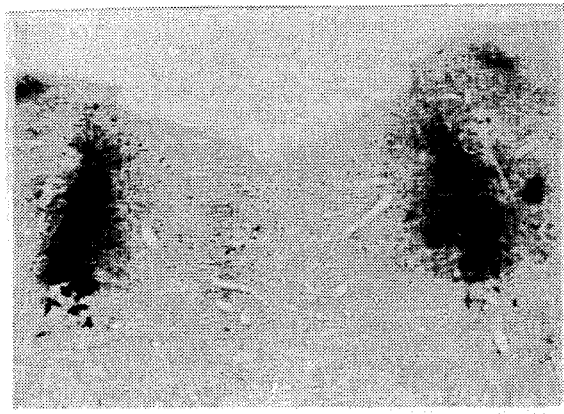
FIG.IIEa
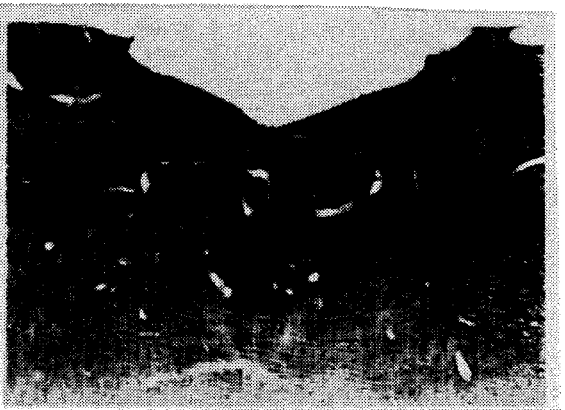
FIG.IIEb
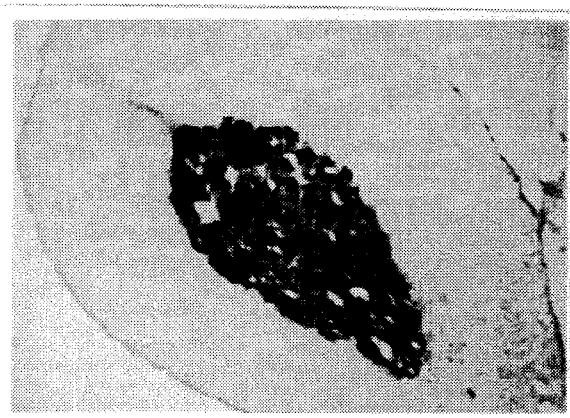
FIG.IIFa
FIG.IIFb

EXPRESSION OF A TARGET GENE IN TRANSGENIC MAMMALS WITH 5' FLANKING SEQUENCES OF THE RAT TYROSINE HYDROXYLASE GENE

This is a continuation of application(s) Ser. No. 07/973,032 filed on Nov. 6, 1992, now abandoned.

FIELD OF THE INVENTION

The present invention relates to expression of a target gene in a transgenic mammal using the regulatory region from the rat tyrosine hydroxylase gene. More specifically, the present invention relates to the use of the 5' flanking sequence of the rat tyrosine hydroxylase gene to express a target gene in the catecholaminergic neurons of transgenic animals, as well as to the immortalization of catecholaminergic cell lines using the 5' flanking sequence to direct expression an oncogene such as the SV40 T antigen oncogene.

BACKGROUND OF THE INVENTION

Expression of tyrosine hydroxylase (TH), the first and rate-limiting enzyme of catecholamine neurotransmitter biosynthesis, is limited to discrete sets of cells in the CNS and PNS. TH neurons of the CNS include the adrenergic and noradrenergic cells in the brainstem, dopaminergic cells of the midbrain and diencephalon (periventricular and hypothalamic nuclei), and the retinal amacrine cells and the dopaminergic cells in the olfactory bulb (OB). In the periphery, TH expression is largely limited to sympathetic ganglia and the adrenal medullary chromaffin cells. These peripheral TH cells are closely related: they derive from a common precursor that originates in the neural crest (Anderson and Axel, Cell, 47:1079–1090, 1986; Anderson et al., J. Neurosci., 11:3507–3519, 1991), and chromaffin cells from neonates can be transdifferentiated into cells that resemble sympathetic neurons by NGF (Aloe and Levi-Montalcini, Proc. Natl. Acad. Sci. USA, 76:1246–1250, 1979; Naujoks et al., Dev. Biol., 92:365–379, 1982; Doupe et al., J. Neurosci., 5:2119–2142, 1985). In contrast, CNS TH neurons arise from independent cell groups during neurogenesis, express TH at different times, and are functionally and anatomically distinct (Specht et al., J. Comp. Neurol., 199:233–253, 1981a; Bjorklund and Lindvail, Handbook of Chemical Neuroanatomy, Vol. 2, pp. 55–122, 1984). The mechanism responsible for TH expression in such disparate cell groups might be expected to rely on multiple regulatory elements, some that may be needed in all TH tissues and others that may mediate expression in a particular cell group.

Previous studies aimed at defining cis-acting DNA elements that direct TH expression have been of two sorts: those performed in vitro in cultured cells and those performed in vivo in transgenic mice. The in vitro work (Cambi et al., J. Neurochem., 53:1656–1659, 1989, the disclosure of which is incorporated by reference herein) compared expression of a chloramphenicol acetyl transferase (CAT) reporter gene under the transcriptional control of 5' flanking TH DNA in a TH-expressing pheochromocytoma (PC) cell line with that in a variety on non-TH-expressing lines. These experiments demonstrated that 212 base pairs (bp) of DNA upstream of the transcription start site were sufficient for TH transcription in PC cells and that sequences between −212 and −187 (where +1 is the start of the transcription) were required (Cambi et al., supra; Fung et al., J. Neurochem., 58:2044–2052, 1992). Further experiments using site-directed mutagenesis to pinpoint functional elements demonstrated that two sites known to bind transcription factors work together to direct appropriate expression in cultured cells (Yoon and Chikaraishi, Neuron, 9:55–67, 1992, the disclosure of which is incorporated by reference herein). One site is an AP1 element (TGATTCA) at −205 that is bound by the members of the FosJun family of transcription factors (Curran and Franza, Cell, 55:395–397, 1988); the other contains an E-box motif (CAXXTG) at −194 that interacts with the transcription factors containing a helix-loop-helix motif like myc, MyoD, the products of achaete-scute, and E2A (Murre et al., Cell, 56:777–783, 1989; Blackwell and Weintraub, Science, 250:1104–1110, 1990). While these experiments provide fine resolution mapping of sites important for transcription in adrenal medullary PC cells, they give no information about tissue-specific expression in the neurons of the CNS or in sympathetic neurons, that is, in true neurons. In addition, the PC lines represent a limited range of developmental stages that may not reflect the mature state of differentiation. Due to the paucity of TH-expressing CNS cell lines, investigations of TH regulation in the CNS have used transgenic mice, where fine mapping is very difficult due to the time and expense involved in maintaining transgenic lines.

Although limited in number, previous experiments in which TH regulatory regions were used in transgenic mice have failed to demonstrate correct tissue-specific expression in all TH cells, although some TH cell groups were appropriately targeted. In a recent study, the human TH gene including the entire coding sequence, 25 kilobases (kb) of 5' flanking region, and 0.5 kb of 3' flanking region, was expressed in transgenic mice (Kaneda et al., Neuron, 6:583–594, 1991). The transgene was expressed in the brain and the adrenal, both TH-expressing tissues. However, primer extension analysis performed on RNA from various brain regions revealed inappropriate expression of human TH message in regions that lack TH-positive cell bodies; these regions included the frontal cortex, striatum, and the hippocampus. In fact, expression in the inappropriate areas appeared at least as strong as expression in TH-positive areas. This study did not examine expression in the sympathetic ganglia or in the main OB.

Similar results were obtained by Morgan and Sharp using sequences from the mouse TH gene linked to β-galactosidase. They reported that transgenic mice carrying 3.5 kb of 5' flanking DNA demonstrated appropriate β-galactosidase expression in the brainstem, midbrain, and adrenal, but ectopic reporter expression in other CNS regions, which may have been due to the site of integration (Morgan and Sharp, Abst. Soc. Neurosci., 17, 1991). Taken together, these studies indicate that none of the transgenic lineages so far examined have demonstrated completely correct tissue-specific expression. In all cases, some appropriate TH-positive cell groups do express the linked reporter, while others do not; in addition, ectopic CNS expression was observed in all three studies.

Immortalized cell lines of differentiated neuronal cell types, including those from the PNS and CNS, can be valuable research tools because they provide homogeneous sources of single cell types. They can be used to elucidate mechanisms of induction without the complicating presence of non-target cells, a situation impossible to achieve in vivo or in mixed primary cultures. They can also serve as sources for cell transplants of cell-specific molecules, as recipients for such molecules in gene transfer experiments or as sources for cell transplants into the nervous system. Neuronal cell lines from the central nervous system (CNS) are especially valuable since it is difficult to prepare our populations of primary neurons. In addition few differentiated cell lines originating from the CNS exist.

Neuronal cell lines have been generated by four methods: 1) from spontaneously arising or chemically induced tumors; 2) by fusion of neurons to neuroblastoma cells; 3) by retroviral infection of neural precursor cells; and 4) by the use of oncogenes driven by cell-specific promoters that direct tumorigenesis to defined neurons in transgenic mice. Although many cell lines have been derived from spontaneous or induced tumors, the majority are relatively undifferentiated (Spengler et al, In Vitro, 8:410, 1973; Schubert et al., Nature, 249:224–229, 1974; Waymire and Gilmer-Waymire, J. Neurochem., 31:693–698, 1978). Many have a mixed neuronal and glial phenotype characteristic of very mature cell types. The PC12 cell line (Greene and Tischler, Proc. Natl. Acad. Sci. USA, 73:2424–2428, 1976) and some mouse C-1300 subclones (Amano et al., Proc. Natl. Acad. Sci. USA, 69:258–263, 1972) do exhibit some differentiated properties. However, all of these are derived from the peripheral nervous system (PNS). Somatic cell hybrids offer the potential for obtaining immortalized cells with a well-differentiated phenotype, since mature neurons can theoretically be used as fusion partners. Unfortunately the success rate of such fusions is low and most researchers have relied on embryonic neuronal tissue to obtain hybrids which resemble mature neurons of varying degrees (Lee et al., J. Neurosci., 10:1779–1787, 1990; Choi et al., Brain Res., 552:67–76, 1991). An additional major drawback of somatic cell hybrid is the extent to which the neuroblastoma partner may influence the resulting hybrid, since the neuroblastoma parent is of PNS origin. This is of concern because hybrids contain additional chromosomes derived from the neuroblastoma parent and often lose those from the non-neuroblastoma parent. Recently, mesencephalic hybrid lines have been established by the fusion of embryonic mesencephalic cells with a neuroblastoma line (Choi et al., supra). Although these lines resemble mature midbrain neurons, they synthesize not only dopamine but also norepinephrine, which is surprising since mesencephalic cells are exclusively dopaminergic (Bjorklund and Lindvall, supra). Some of these problems can be circumvented by generating cell lines with retroviral or transgenic technologies. Retroviral infection of primary neuron cultures can result in neuronal cell lines capable of undergoing differentiation under appropriate conditions (Cepko, Ann. Rev. Neurosci., 12:47–65, 1989; Lendahl and McKay, Trends Neurosci., 13:132–137, 1990). Since the virus requires at least one round of cell-division in order to integrate into the host's genome, this approach has been largely limited to immortalization of cycling precursor cells (Fredericksen et al., Neuron, 1:439–448, 1988; Ryder et al., J. Neurobiol., 21:365–375, 1990). Transplantation experiments have shown that these precursor cells retain their plasticity when implanted into a developing brain, giving rise to cells appropriate for the site of implant (Renfranz et al., Cell, 66:713–729, 1991). Retroviral infection has thus been of greatest use for lineage analyses and other developmental studies.

The most direct approach to create cell lines of defined neuronal cell types utilizes tissue-specific promoter elements to direct oncogene expression in transgenic mice (Cory and Adams, Ann. Rev. Immunol., 6:25–48, 1988; Jenkins and Copeland, *Important Advances in Oncology*, Ed., 61–77, 1989, the disclosure of which is incorporated herein). In this way, very specific cells may be targeted. In the last few years this technique has led to the immortalization of gonadotropin releasing hormone (GnRH)-expressing and retinal amacrine neurons (Mellon et al., Neuron, 5:1–10, 1990; Hammang et al., Neuron, 4:775–782, 1990; Messing et al., 1991, Soc. for Neurosci., abstract #21.11), as well as differentiated cells of many non-neuronal tissues (Hanahan, Nature, 315:115–122, 1989). Since the target cell destined for transformation is determined by the regulatory promoter elements used, in theory, tumors can be induced in any cell type for which specific regulatory elements are available. For the most part, tumors have been observed in the appropriate tissues, although ectopic expression does occur (Cory and Adams, supra; Behringer et al., Proc. Natl. Acad. Sci. USA, 85:2648–2652, 1988).

Thus, it would be desirable to provide a full repertoire of TH-expressing cells which express a target gene under the control of a regulatory region which permits correct expression in such cells. Similarly, it would be desirable to immortalize such cell lines under the control of a regulatory region which drives an oncogene and which permits correct expression.

SUMMARY OF THE INVENTION

In accordance with one embodiment of the present invention, there is provided expression of a target gene in a transgenic mammal by employing the 5' flanking sequence of the rat tyrosine hydroxylase gene. More specifically, it has been found that target genes can be expressed in the catecholaminergic neurons of transgenic mammals by employing from greater than about 0.3 kb to at least about 4.8 kb of the 5' flanking sequence of the rat tyrosine hydroxylase gene.

In another embodiment of the present invention, there is provided immortalized catecholaminergic neuronal cell lines from transgenic mammals which include the 5' flanking sequence of the rat tyrosine hydroxylase gene which directs expression of an oncogene such as the SV40 T (Tag) antigen oncogene. The immortalized cell lines of this invention can be used for a number of purposes, including, for example, the screening of drugs, i.e., agonists or antigonists, for neurotransmitter ligands or neurotransmitter receptors (glutamate receptors, dopamine receptors, nicotine acetylcholine receptors, and the like) or ion channels which neuronal cells bear. Immortalized cell lines may also be used as donor cells in neurotransplants, into which exogenous genes such as trophic hormones, toxic genes, and the like can be introduced and expressed in a stable fashion. These cell lines will also serve as a homogenous source of proteins endogenous to catecholaminergic neuronal cells such as neurotransmitters, growth factors, growth factors receptors, transporter molecules, neurotransmitter receptors, and the like.

The present invention also relates to vectors into which is inserted the 5' flanking sequence of the rat tyrosine hydroxylase gene operably linked to a polylinker containing at least one restriction site.

BRIEF DESCRIPTION OF THE DRAWINGS

FIG. 1 is a map of the –4.8 THCAT. The lower part depicts the restriction map of the TH sequences present in the transgene.

FIGS. 4A–4C is a map of the 4.8TH plasmid: 4A) 4.8THO; 4B) 4.8TH-GH; and 4C) 4.8TH-Tag.

FIGS. 11A–11F illustrate the staining of HGH in the TH expressing regions of the CNS of TH-GH transgenic mice. The left photograph in each panel (FIGS. 11Aa–11Fa) is staining with anti-growth hormone antibody, the right panel (FIGS. 11Ab–11Fb) with anti-TH antibody to show that the TH cells also stain for growth hormone. The left and right panels are adjacent sections. 11A) olfactory bulb; 11B) diencephalon, the narrow bar is the arcuate nucleus of the hypothalamus, the wide bar is the A13/A11 hypothalamic region; 11C) caudal A11; 11D) midbrain (mesencephalon), narrow bar indicates the ventral tegmental area (VTA), narrow bar indicates the substantia nigra; 11E) locus coeruleus in the pon-medulla; and 11F) adrenal gland.

DETAILED DESCRIPTION OF THE INVENTION

Figure 2:
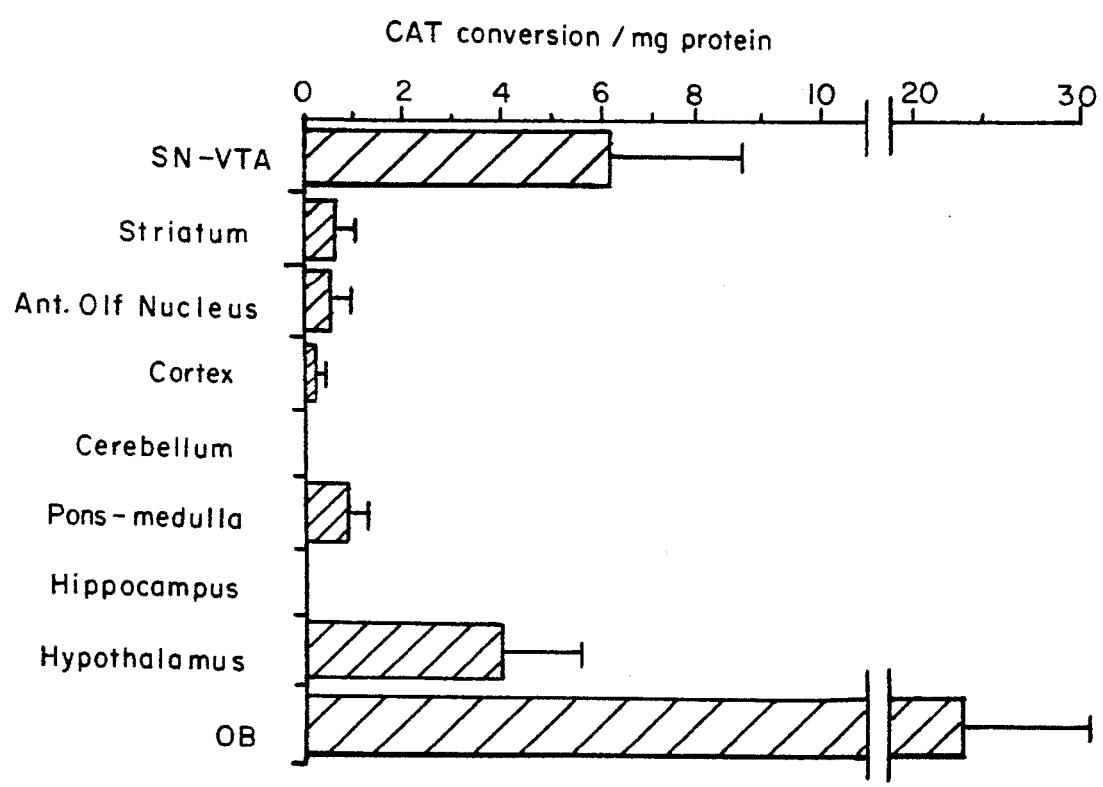
FIG. 2 illustrates the specificity of CAT expression in dissected brain regions. CAT assays were performed on extracts made from dissected regions from transgenic mice >60 d old as identified previously by dot blots. Up to 200 μg of protein was used for each assay. Each bar represents a mean ±SEM of CAT assays from four transgenic animals.

In accordance with one embodiment of the present invention there is provided a transgenic mammal capable of expressing a target gene in catecholaminergic neuronal cells by employing the 5' flanking sequence of the rat tyrosine hydroxylase gene (hereinafter sometimes referred to as the "5' flanking sequence"). More specifically, there is provided the means for expressing a target gene using the 5' flanking sequence in the full repertoire of catecholaminergic neuronal cells (sometimes also referred to as "TH-expressing" cells).

In accordance with the present invention, it has been found that from greater than about 0.3 kb to at least about 4.8 kb of the 5' flanking sequence may be used to express target genes in transgenic mammals, including mice, rats, pigs, and the like. Regions greater that 4.8 kb, while not preferred, may also be used as long as there is no substantial interference with expression of the target gene.

In order to efficiently target many different genes under the control of the 5' flanking sequence, a construct 4.8THO was created that facilitated these constructions which had a linker region with unique restriction sites positioned downstream of the TH 5' region. Various target genes can be inserted to the unique Sma I, Nru I and Sal I sites such that they will be under the transcriptional control of 4.8 KN to +10 bp of the rat TH regulatory region. As will be appreciated by the skilled artisan, the 5' flanking sequence and polylinker may be inserted into other vectors. The plasmid 4.8THO was created from 4.8THCAT by replacing the region between the −19 (Nar I site) and +2562 (Nar I site, which is the unique Nar I site in pUC vectors at position +235, Yanisch-Perron et al., Gene, 33:103, 1985) with a synthetic linker sequence containing TH sequences from −18 to +10 followed by cloning sites for the restriction enzymes Sma I, Nru I and Sal I. A sample of 4.8THO was deposited at the American Type Culture Collection on Nov. 6, 1992 under ATCC Accession No. 75343. The sequence of the linker is 5' CGCCTGCCTGGCGAGGGCTGTGGAGA-CACCCGGGTGG 3' (SEQ. ID NO. 1). Two copies of the linker were inserted such that the 4.8THO plasmid contains rat TH sequences between −4.8 kb to +10 bp, followed by two copies of the linker sequence, which end by reconstructing the Nar I site in the puC vector at +235. The remainder of the plasmid consists of pUC vector sequences from position +235 to the polylinker region and extending into the pUC polylinker region with Hind III and Eco RV and Eco RI sites. The Eco RI starts the rat TH genomic DNA at about −4.8 kb. The plasmid retains an ampicillin resistance gene and a Col E1 origin of replication.

The transgenic host containing the target gene under the control of the 5' flanking sequence may be produced in a number of ways, as described in Hogan et al. (*Manipulating the Mouse Embryo: A Laboratory Manual,* Cold Spring Harbor Labs., CSH, N.Y., 1986), the disclosure of which is incorporated by reference herein.

In general, in accordance with the present invention, when working with mammals, one would link the 5' flanking sequence to the target gene in an appropriate vector or plasmid. Thereafter, one would preferably eliminate plasmid sequences from the target gene/5' flanking sequence prior to injection into the fertilized mammalian host cells by isolating a specific linear DNA fragment. The appropriate fragment is typically obtained by gel purification and thereafter injected into fertilized mammalian host cells. Transgenic positive animals may be identified by any suitable technique, for example, by dot blots or Southern blots or PCR (polymerase chain reaction) of DNA obtained from biopsies.

Virtually any target gene can be expressed in catecholaminergic neuronal cells using the 5' flanking sequence in accordance with the present invention.

Successful expression of the target gene will require or depend on a number of factors including whether the transgene is integrated into a chromosomal region that is able to be transcribed, whether the protein product is stable in the particular cell, whether the host cell has the appropriate factors to transcribe the transgene, whether the transgene is intact, and what regulatory regions are used.

General Considerations When Constructing Target Genes Under the Control of the Rat TH Regulatory Region Optimally, the targeting constructs should include: rat TH enhancer elements and the rat TH promoter and the rat TH RNA initiation region (around the +1 position). The translational initiation site optimally should be provided by the target gene. If the target gene lacks the translational signals needed for efficient translational initiation in mammalian cells, which would be the case for bacterial target genes, the translational initiation site from a mammalian gene which is efficiently translated should be substituted for that of the target gene. After the translational termination site, the target gene should contain a consensus polyadenylation site to allow efficient polyadenylation in mammalian cells.

For example, one may wish to express human growth hormone (HGH) in these neuronal cells in order to assess in which cell types the targeted transgene like growth hormone is expressed. A target gene that can be detected histologically is advantageous, since its presence can be localized to individual cells. Unfortunately, the bacterial chloramphenicol aceytlytransferase gene, a commonly used target, cannot be efficiently detected histologically. In an organ such as the brain, which is composed of many different types of neurons, the ability to localize transgene to individual cells is crucial to assessing if the transgene is correctly targeted. Therefore, the human growth hormone gene could be inserted into the 4.8THO plasmid. Since commercially available antibodies (from Amel) to human growth hormone can be used to detect growth hormone in tissue sections, it serves as a good histologically-detectable transgene. In addition, it can be quantitated by radioimmune assay using commercially available kits from Allegro or Hybritech in tissue extracts.

In addition to assessing the specificity of transgene expression, the resulting animals could be used to study the effect of growth hormone expression in the catecholaminergic neurons of the CNS and in the chromaffin cells of the adrenal medulla. One potential use would be to create a new model of growth hormone deficiency by expressing human growth hormone in the hypothalamus of transgenic mice.

Similarly, one could express a nucleotide sequence or gene coding for a toxin, such as Diptheria Toxin A (Maxwell et al., Mol. Cell. Biol., 7:1576–1579 (1987), the disclosure of which is incorporated by response herein), also described in the Examples which follow.

Neuronal cells, including catecholaminergic cells, which express the target gene may be determined by assaying the presence of the target gene by antibody staining or enzymatic activity of a target gene, in situ hybridization analysis, or in the case of a toxic gene, by the absence of TH-expressing neurons.

In general, current evidence shows that the rat 4.8 kb of 5' flanking DNA directs perfect target reporter gene expression to all TH expressing CNS neurons to the adrenal chromaffin cells (see Examples 1 and 2, infra). Shorter 5' constructs (between 2.8 and 0.773 kb) give expression that is appropriate for some TH expression regions, but not all TH expression cell groups. The exact sites in which expression is observed with these shorter constructs is somewhat variable. Example 5 (infra) discloses that 0.773 and 2.8 kb of sequence gives expression in the adrenal, midbrain and pons-medulla, but not in the sympathetic ganglia or in the olfactory bulb. (Joh et al., Abstr. Soc. Neurosci., 18:239, 1992) used 2.4 kb of rat TH 5' DNA and observed reported gene expression in the olfactory bulb, the midbrain and the locus coeruleus, but not in other TH expressing CNS neurons (such as those of the diencephalon) and not in the adrenal chromaffin cells. Therefore, the exact pattern of expression using constructs between 0.773 and 2.8 kb may vary with the exact sequence of the region used. The shortest constructs that have been examined, 0.272 (Example 1, infra) and 0.150 (Joh et al., supra) kb of TH 5' DNA do not support reporter gene expression in any tissue examined.

Figure 4A:
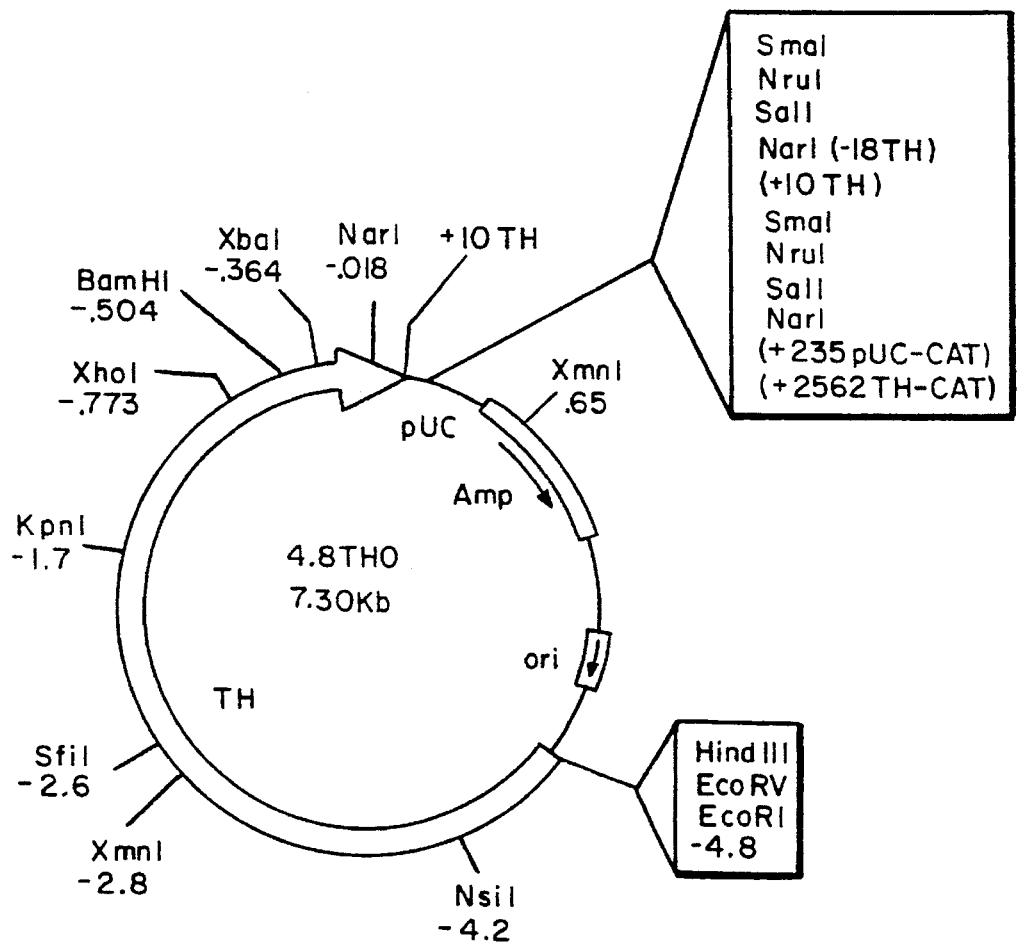
Figure 4C:
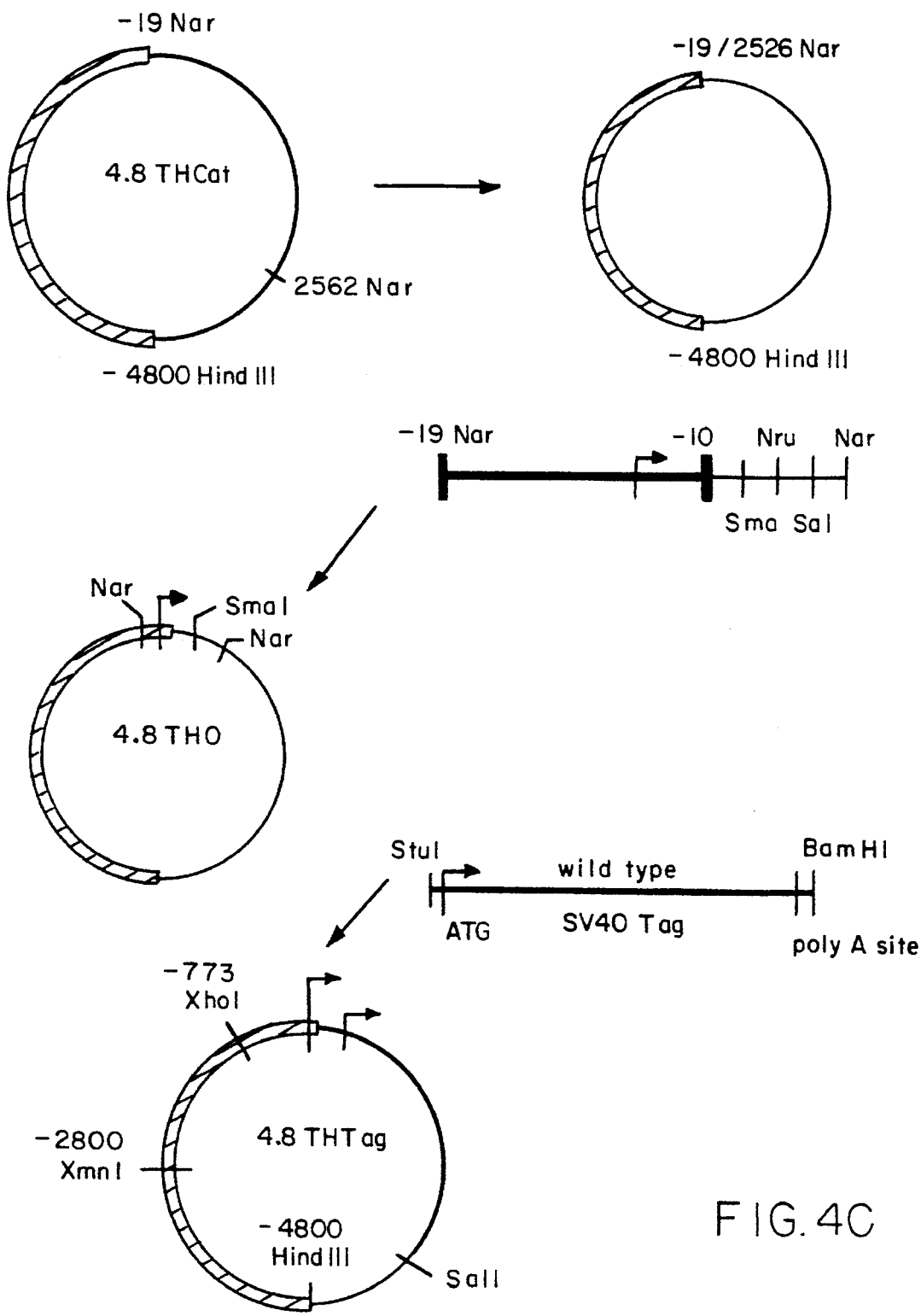
Figure 5A:
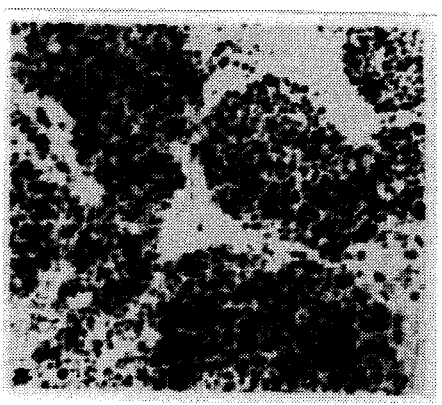
FIGS. 5A–5E illustrate a typical staining pattern for the TH and Tag proteins in adrenal and brain tumor sections.
Figure 5B:
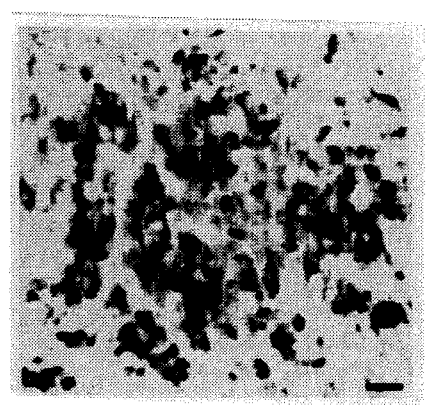
Figure 5C:
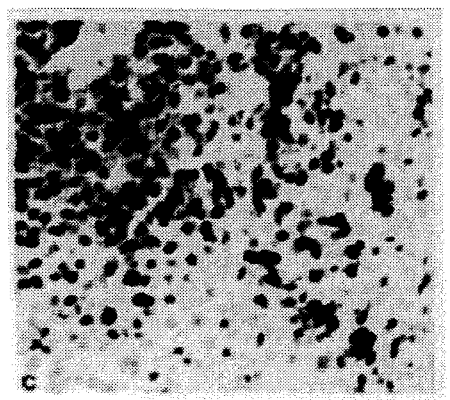
Figure 5D:
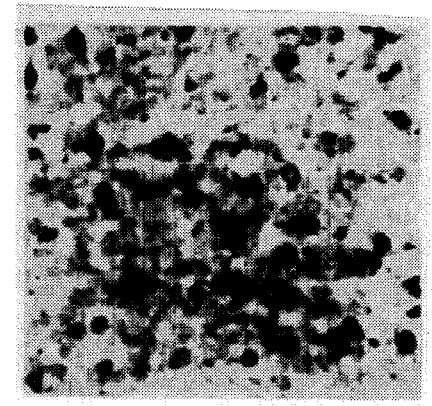
Figure 5E:
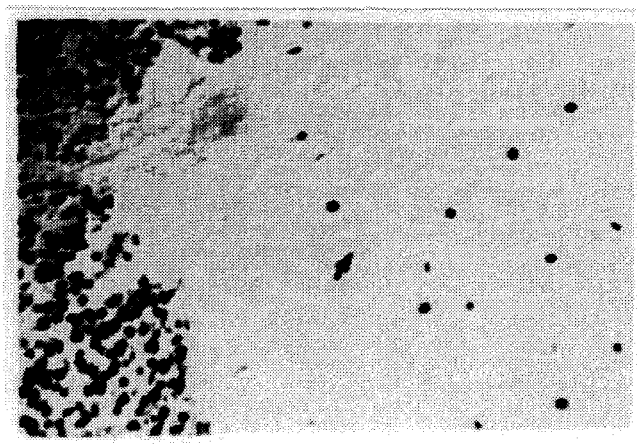

To determine the expression pattern for any given length of 5' flanking DNA used in transgenic animals, one could create varying lengths by cutting with suitable restriction enzymes that cleave in the 4.8 TH region (See FIGS. 1 and 4 which show some of these sites). Both 5' deletions and internal deletions could be generated. The resulting regulatory DNA could be inserted in front of a suitable reporter gene such as CAT, human growth hormone, beta galactosidase, etc., and the resulting transgenic mammals assayed for transgene expression as described in Example 1 or 2 (infra).

In accordance with another embodiment, there is provided immortalized catecholaminergic neuronal cells. Immortalized catecholaminergic neuronal cells may be prepared by introducing the 5' flanking nucleotide sequence of the rat tyrosine hydroxylase gene and an appropriate oncogene into the target animal.

A generalized protocol for use of the TH regulatory region to direct tumorigenesis to TH expression neurons and TH expression adrenal chromaffin cells in transgenic mice from which neuronal cell lines could be derived is as follows: Various lengths of the regulatory region from the TH gene could be used to direct expression of various oncogenes (see Adams and Cory, supra) to various TH expression cells in transgenic mice. The location of the resulting tumors will generally depend on the exact TH regulatory sequences used. For example, using 0.773 kb (−773 to +10) kb of TH regulatory region, which includes some TH enhancer elements as well as the TH promoter and TH RNA initiation site, oncogene expression (SV40 T antigen, encoded by the Stu I-Bam HI fragment) was detected in the CNS and adrenal, where tumors arose after the mice were 2 months of age. The location of the CNS tumors was consistent with tumorigenesis of neurons of the brainstem (pons-medulla). The resulting cell line (CATH-a) has properties (such as norepinephrine synthesis) consistent with immortalization of TH expression neurons of the pons-medulla. Using 4.8 kb of TH regulatory sequence, all TH expression neurons should be susceptible to tumorigenesis since data show that 4.8 kb of TH upstream DNA directs non-oncogene target gene expression to all of the correct CNS TH-expressing cells with no ectopic expression in the non-TH cells. See Examples 1 and 5, infra.

If the expression of the oncogene is deleterious to the proper development of the transgenic mice, a different or disabled oncogene could be used in place of the wild type oncogene. One such possibility would be the use of a temperature-sensitive oncogene, which is largely inactivated at the body temperature of mammals. Tissues bearing TH-expressing cells could be dissected from the temperature-sensitive oncogene-targeted mice, and incubated at low temperature in tissue culture such that the oncogene would be active and could function to immortalize the cultured cells. A temperature-sensitive T antigen (tsA58) has been used to immortalize epithelial cells from transgenic mice (Jat et al., Proc. Natl. Acad. Sci. USA, 88:5096–5100, 1991, the disclosure of which is incorporated by reference herein). The same temperature sensitive gene could be used as a target for the TH regulatory region.

As with the previously described preferred embodiment greater than about 0.3 to at least about 4.8 kb of the 5' flanking sequence may be used to immortalize cell lines. The 5' sequence used will depend on which neurons are to be targeted and the particular integration site into which an individual transgene is integrated in a given lineage.

Oncogenes which may be employed include those described in Table 1 of Adams and Cory, Science, 253:1161–1167, 1991, including a JCV gene and an HTLV tat gene. The oncogene may be inserted in an appropriate plasmid construct such as the THO 4.8 at an appropriate polylinker site.

The following Examples are provided to further illustrate the invention.

EXAMPLE 1

Generation of Transgenic Mice Containing 5' Flanking Nucleotide Sequence from the Rat Tyrosine Hydroxylase Gene Linked to The Bacterial CAT Gene Materials and Methods The plasmid −4.8 THCAT (FIG. 1) has been previously described (Cambi et al., supra). A Sprague-Dawley rat genomic DNA library in lambda Charon 4A created by T. Sargent and J. Bonner (California Institute of Technology) was screened with a cDNA clone for rat tyrosine hydroxylase, which is isolated by Lewis et al. (J. Biol. Chem., 258:14632–14637, 1983). A TH genomic clone described in Harrington et al. (Nucleic Acids Research, 15:2363–2384, 1987) was isolated that contained sequences from −4.8 kb to about +4.7 kb, with +1 site being the first nucleotide in rat TH mRNA. A plasmid, −773TH-CAT, which contained TH DNA from −773 bp to +27 bp (whose sequence is reported in Lewis et al., Proc. Natl. Acad. Sci. USA, 84:3550–3554, 1987) linked to the bacterial chloramphenicol gene was constructed from subclones of the genomic TH DNA as described (Lewis et al., supra) using a pUC13-CAT vector commercially available from IBI. By replacing the −0.773 kb to −0.364 TH DNA in −773TH-CAT with a longer TH DNA fragment from −4.8 kb to −0.364 kb, generated by restriction of the −4.8 to +4.7 kb lambda genomic clone with Eco RI (at −4.8 kb) and Xba I (at −0.364 kb), 4.8 TH-CAT was created. The fragment injected in B6XLT/SV F1 fertilized eggs in order to generate the −4.8 THCAT lines of transgenic mice was the 6.7 kb HindIII-ApaI fragment that included the CAT gene, the SV40 polyA, and splice sites. Transgene-positive animals were identified by dot blots or Southern blots of DNA obtained from tail biopsies. The radioactive probe used was generated by random primed synthesis from the plasmid pucCAT. Subsequent transgenic progeny were bred with B6D2 F1 hybrid animals (Taconic) to maintain transgenic lines.

CAT assays. Tissues were excised and quickly frozen on dry ice and stored at −70° C. until further use. Tissue extracts were made by homogenization in 250 mM Tris, 1 mM EDTA, pH 7.6. These were heated at 65° C. for 5 min to inactivate deacetylases (Mercola et al., Science, 227:266–269, 1985, the disclosure of which is incorporated by reference herein). The insoluble fraction was removed by centrifugation, and the supernatant was used in the assay. Assays were performed in 180 µl volume-containing final concentration of 3.3 mM acetyl coenzyme A (Pharmacia) and 0.5 µCi of 14C-chloramphenicol (New England Nuclear; 54.9 mCi/mol), 250 mM Tris, and 1 mM EDTA. Reactions were incubated overnight at 37° C. and then extracted with ethyl acetate. Thin-layer chromatography and autoradiography were performed on these samples to separate and visualize the acetylated and unacetylated forms of chloramphenicol. The spots corresponding to each form on the thin-layer chromatography plate were counted in a scintillation counter in order to determine the percentage conversion of chloramphenicol to its acetylated forms. Protein assays were performed using the MicroBCA reagent (Pierce). For brain, liver, heart, kidney, and spleen, 60 µg of protein was used in each assay. For superior cervical ganglion (scg) and adrenals, up to six organs were pooled for each assay; that is, approximately 200–300 µg of protein was used in each assay. The olfactory bulb determinations were carried out on single bulbs.

Dopamine assays. Dopamine from bulbs was analyzed by HPLC followed by electrochemical detection (HPLC-ECD) as previously described (Kawano and Margolis, J. Neurochem., 39:342–348, 1982, the disclosure of which is incorporated by reference herein), with modifications. Briefly, OBs from the killed animals were excised and immediately homogenized in 200 µl of 0.1M $HClO_4$, 1 mM EDTA. After centrifugation of these extracts, the supernatant (the acid extract) was frozen until further use. After thawing, Tris (pH 8.6) was added to 0.67M and the extract was adsorbed onto an alumina minicolumn to bind the catechol amines. Columns were washed twice with ice-cold water and then eluted with 120 µl of 0.4M $HClO_4$, 0.1 mM EDTA. Eluents were then injected onto a reverse-phase C-18 column (Beckman), and catechols were detected by a Bioanalytical Systems model 460 liquid chromatograph with an electrochemical detector. The mobile phase contained 50 mM $NaH_2PO_4$, 0.387 mM sodium octyl sulfate, 0.1 mM EDTA, and 5–7.5% methanol, and the flow rate was maintained at 1.5 ml/min.

TH assays. TH enzyme activity was analyzed from various organs as described before (Rittenhouse et al., Neuroscience, 25:207–215, 1988, the disclosure of which is incorporated by reference herein), with slight modifications. Excised tissues were homogenized in cold 5 mM Tris, 0.1% Triton X-100, pH 6.0. After centrifugation, 10 µl of homogenate was used per assay. These assays were performed in 20 µl volume, containing a final concentration of 300 µM brocresine (an inhibitor of dopa decarboxylase), 80 mM tyrosine, 40 mM β-mercaptoethanol, 3.2 mM 6-methyl-5,6, 7,8-tetrahydropterine, $2 \times 10^5$ U/ml catalase, and 200 mM potassium phosphate buffer, pH 6.0 for 6 min at 37° C. The reaction was stopped with addition of 1 ml of 0.5M Tris (pH 8.6) containing 0.1 mM EDTA, and the dopa generated was adsorbed onto alumina columns and washed twice with cold 1 mM $NaHSO_3$, 5 mM Tris (pH 8.6). The dopa was eluted in 100 µl of 150 mM $H_3PO_4$, 0.1 mM EDTA from the column and detected by HPLC-ECD as described above. Protein content in the homogenates was determined by the MicroBCA reagent (Pierce).

Deafferentation. A single intranasal dose of 50–100 µl of solution was administered to unanesthetized mice (≧60 d of age) using a syringe needle that was clipped to approximately 3 mm in length and filed to a blunt end. Experimental mice received 0.17M $ZnSO_4$ in 0.15M NaCl, and control mice received saline. The mice were killed 8 d following this procedure and single OBs were used for CAT assays and dopamine assays.

Results

Transgenic analysis

Since cell culture experiments suggests that only 212 nucleotides of the 5' flanking sequence of the rat TH gene were required to confer expression in PC cells, we generated three transgenic lines bearing 272 nucleotides of TH upstream sequence linked to a CAT reporter gene. The founders and two generations of progeny were analyzed for transgene expression. None of the animals expressed CAT activity in any tissue including TH-positive regions. It is not clear whether this was due to a lack of sequences important for in vivo expression, or whether all three lines were nonexpressors due to integration site effects. For this experiment, we therefore generated transgenic founders carrying a much larger piece of DNA, that is, 4.8 kb of 5' flanking TH sequence. This construct utilized the TH transcriptional start site (+1), the CAT translational initiation site, and the SV40 polyA and splice sites (FIG. 1), such that the CAT gene was under the transcriptional control of the TH 5' sequences.

Four transgenic founders were obtained that carried an unrearranged transgene determined by Southern blot analysis.

TABLE 1

*Tissue-specific CAT and TH activity in −4.8 THCAT mice

| Tissue | CAT (% conversion/ mg protein) | TH activity (pmol dopa/mg protein/min) | CAT/TH ($\times 10^{-2}$) |
|---|---|---|---|
| OB | 26.7 ± 10 | 152.3 ± 53.2 | 17.5 |
| scg | 8.33 ± 2.0 | 1667 ± 523 | 0.5 |
| Brain | 0.67 ± 0.5 | 38.7 ± 1.2 | 1.73 |
| Adrenal | 2.83 ± 0.5 | 2915.6 ± 706 | 0.1 |
| Liver | ND | NT | |
| Heart | ND | NT | |
| Spleen | ND | NT | |
| Kidney | ND | NT | |

*Extracts from the CAT assays were made from ≧60-d-old animals identified as transgenic by dot blot assays. For all negative tissues and for brain, individual assays were performed on a small fraction of the extract made from a single organ. For the adrenal and scg, four to six organs were pooled for individual assays. For the OB, individual assays were performed on whole bulbs. Numbers are mean CAT activities from these individual assays ± SEM. Protein assays were performed using the MicroBCA reagent (Pierce). TH assays were performed on transgenic animals and on their nontransgenic littermates, with no significant difference between the two groups. All assays were performed on extracts from single organs (see Materials and Methods). TH assays were not performed on liver, heart, spleen, or kidney, which lack TH activity. Protein assays were performed by the method of Lowry. ND, Not detectable; NT, not tested.

Only one line expressed the transgene and was therefore analyzed. The founder was apparently a germline chimera since only 3 out of 24 F1 progeny inherited the transgene. In subsequent generations, the transgene was present in a single copy, which was inherited in a Mendelian manner consistent with an autosomal site of integration. During the course of this study, over 75 transgenic mice from eight generations were analyzed. In all cases, expression of the transgene was detected with no extinction in any of the progeny. In addition, transgene expression, as quantitated by CAT activity, was dose dependent, with homozygotes showing a twofold higher level of CAT expression than heterozygotes (data not shown). The animals reported here were all heterozygous for the CAT transgene.

Tissue-specific expression

Tissue extracts were prepared from TH-positive tissues: whole brain excluding the OB (henceforth referred to as "brain"), the OB, a sympathetic ganglion (the scg), and the adrenal glands, as well as from TH-negative tissues like the heart, liver, kidney, and spleen. CAT activity was detected in all tissues in which TH cells are found, although it is very low in whole brain, due to the dilution of the CAT-expressing cells with nonexpressing cell types (Table 1). No activity was seen in any TH-negative tissue. To assess how the activity of the CAT reporter compared to endogenous TH activity, TH assays were performed on the all TH-positive tissues (Table 1, column 2). Since TH assays were performed in vitro under fully activating conditions, activity should reflect TH protein levels. When CAT levels were normalized to endogenous TH enzyme activity, the adrenal showed lower CAT activity than would be predicted based on its endogenous TH enzyme activity (Table 1, column 3). This was also true for scg, although to a lesser extent. In addition, TH activities from the brain, adrenal, scg, and OB of nontransgenic animals were not significantly different from those of transgenic animals, suggesting that transgene expression did not alter the expression of endogenous TH (data not shown).

These data demonstrate that 4.8 kb of 5' flanking TH sequence is sufficient to direct appropriate tissue-specific expression of CAT, but at a lower level in the periphery than would be predicted by endogenous TH activity.

CAT expression in various brain regions

To determine if the expression of CAT within the brain was restricted to the regions known to contain TH-positive cells, we assayed CAT activity in dissected brain regions. Since CAT is a bacterial protein and presumably lacks axonal transport signals, most of the protein should remain in the cell bodies of TH-expressing neurons. Therefore, we assayed CAT activity in extracts from regions containing TH-positive cell bodies such as the ventral midbrain (containing the ventral tegmental area and the substantia nigra; SN-VTA), pons-medulla (containing the locus coeruleus and the lateral tegmental area), and hypothalamus. Areas that have no TH-positive cell bodies but receive catecholaminergic projections were also assayed. These included the hippocampus, striatum, cerebellum, anterior olfactory nucleus (AON), and cortex.

All areas containing TH-positive nuclei showed significant levels of CAT activity (FIG. 2). A much lower level of activity was observed in some areas like the striatum and the AON, which contain no TH-positive cell bodies but are heavily innervated by projections from TH-positive cells. Sparsely innervated regions such as the cortex and hippocampus showed levels of activity that were statistically background. It is likely that a small amount of CAT protein is found in the axoplasm in areas innervated by TH cells resulting in the low activity observed in heavily innervated regions. However, the possibility that there are a small number of cells in these regions that are ectopically expressing CAT cannot be ruled out, since CAT cannot be localized by immunohistochemical methods.

Developmental regulation of CAT in the OB

To determine whether 4.8 kb of 5' flanking rat TH DNA could direct accurate developmental expression, we assayed for CAT activity in OBs of transgenic animals at various times after birth. Unlike most other TH-positive neurons, the onset of TH expression in the OB is almost entirely postnatal. TH-positive neurons of most catecholaminergic groups in the rat brain are present by E14.5; in contrast, TH-immunoreactive cells first appear in the OB at E21, shortly before parturition, and continue to increase until 2 months after birth (Specht et al., 1981a, supra, and Specht et al., J. Comp. Neurol., 199:255–276, 1981b; McLean and Shipley, J. Neurosci., 8:3658–3699, 1988, the disclosure of which is incorporated by reference herein).

Figure 3A:
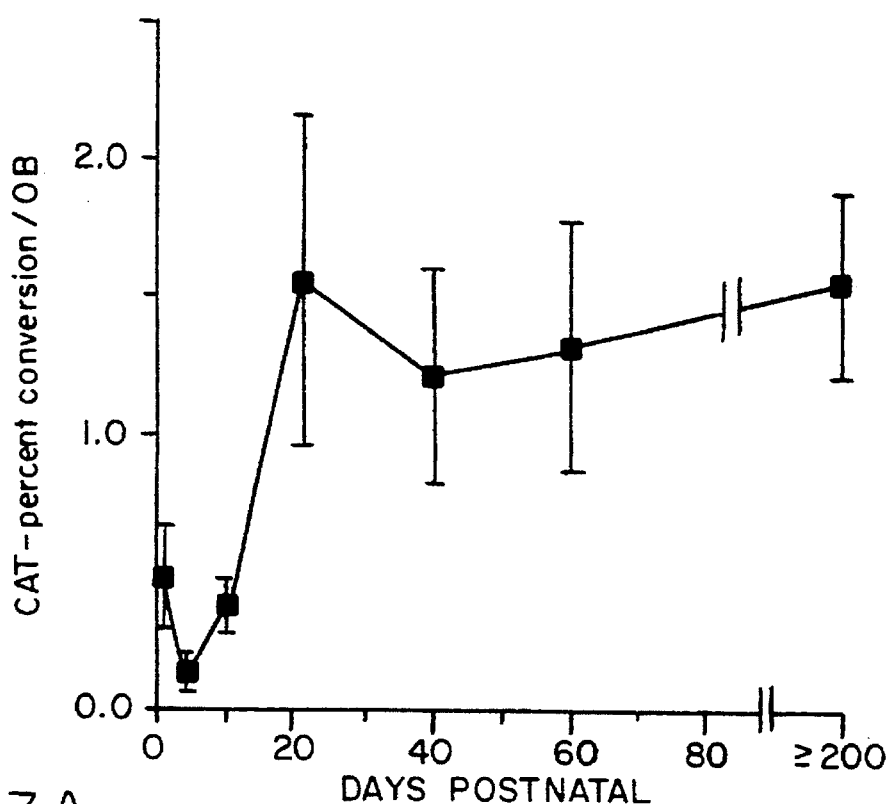
FIGS. 3A and 3B illustrate CAT and TH development in transgenic and nontransgenic mice. A. Developmental expression of CAT in the OB of transgenic mice. CAT assays were performed on single bulbs of transgenic mice previously identified by dot blots, on postnatal days, 1, 4, 10, 21, 40, and >60. Each point represents mean ±SEM assays on four or five mice. ANOVA analysis of the data revealed that CAT levels at postnatal 21 days were significantly different from those at day 1, day 4, and day 10, but not at day 40, day 60, or day >200 ($p < 0.05$). B. Developmental expression of TH in the OB of transgenic mice and their nontransgenic littermates. TH assays were performed on the remaining OB of the same animals used for CAT activity at postnatal days 1, 4, 10, 21, 40, 60, and >200. Two or three transgenic mice and two or three nontransgenic littermates were used for each time point. Since no significant difference was observed, the data were pooled. Each point represents mean ±SEM of assays on four to six mice. ANOVA analysis of the data revealed that TH levels at postnatal day 21 were significantly different from those at day 1, day 4, and day 10, but not at day 40, day 60, or day >200 ($p < 0.05$).
Figure 3B:
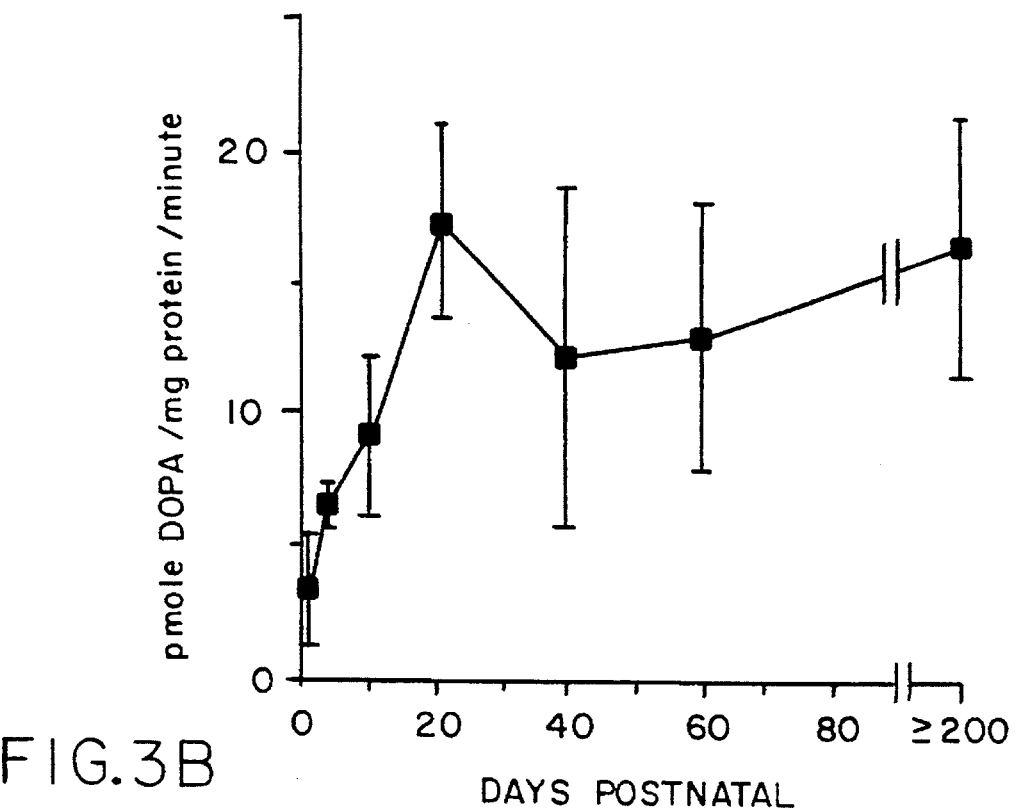

Because of the robust CAT activity in the OB, we were able to quantitate CAT levels from a single bulb, using the other bulb for TH activity. As shown in FIG. 3A, CAT expression increased steadily until day 21, after which there was no further increase. The rise in CAT activity coincided closely with that of endogenous TH, which also increased until postnatal day 21 (FIG. 3B). The large standard deviations observed at each time point are probably the result of the mixed genetic background of individual progeny, caused by breeding of the transgenic animals to B6D2 hybrids at every generation. It has previously been shown that significant strain-specific differences exist in the levels of TH in the brain (Reis et al., Catecholamines: Basic and Clinical Frontiers, Vol. 1, pp. 23–33, 1978). Nevertheless, the developmental pattern of CAT expression parallels that of endogenous TH activity, suggesting that 4.8 kb of upstream region of TH sequences directs appropriate developmental regulation in the OB.

Transsynaptic regulation in the OB

To determine whether our construct could mediate responsiveness to an authentic transsynaptic stimulus, we examined the dependence of CAT on afferent innervation in the OB. This paradigm was studied for three reasons. First, because robust expression of CAT was observed in the OB, transgene expression could be assayed in single animals. Second, the OB is a well-studied model for the transsynaptic regulation of TH. Finally, these studies would allow a functional demonstration of CAT expression in the appropriate subset of cells in the OB, since deafferentation specifically affects the TH-positive cells in the OB.

TH in the OB is expressed in the periglomerular and external tufted cells (together known as the juxtaglomerular neurons), which receive afferents from olfactory neurons whose cell bodies reside in the nasal epithelium. Expression of TH in these OB neurons requires that these inputs be intact (Baker et al., J. Neurosci., 3:69–78, 1983, the disclosure of which is incorporated by reference herein). If destroyed, TH activity

TABLE 2

*Regulation of CAT activity in response to deafferentation

| Animals | n | CAT activity (conversion/ bulb ± SD %) | Dopamine (pmol/ bulb ± SD %) |
| --- | --- | --- | --- |
| Transgenic, untreated | 6 | 1.4 ± 0.34 | NT |
| Transgenic, deafferented | 8 | 0.56 ± 0.17 | 1.5 ± 0.41 |
| Transgenic, saline treated | 8 | 1.37 ± 0.5 | 4.94 ± 1.78 |
| Nontransgenic, saline treated | 4 | ND | 5.36 ± 1.38 |

*Animals that were ≧60 d old were subjected to an intranasal lavage with 50–100 μl of 0.17M ZnSO$_4$ in 0.15M NaCl or with saline alone. Both sets were killed 8 d following treatment. CAT activity was assayed from the left OB and dopamine assays were performed on the right bulb of each animal. The number of animals used in each category is denoted by n. ND, Not detectable; NT, not tested.

(Baker et al., Brain Res., 450:69–80, 1988), immunoreactivity (Baker et al., 1983, supra, and Baker et al., Neuroscience 3:605–615, 1984), and RNA (Ehrlich et al., Mol. Brain Res., 115–222, 1990, the disclosure of which is incorporated by reference herein) are severely reduced. Although deafferentation induces the loss of TH, the juxtaglomerular neurons do not die and can be detected by the continued presence of dopa decarboxylase (Baker et al., 1984, supra, the disclosure of which is incorporated by reference herein).

Because TH is specifically lost after destruction of direct synaptic inputs to the juxtaglomerular neurons, it is likely that ectopically expressed CAT, that is, nonjuxtaglomerular neurons, would not be reduced by deafferentation. It was therefore expected that CAT would be transsynaptically regulated only if expressed in the TH-expressing cells of the bulb and if our construct contained sequences capable of mediating this effect. We therefore assayed the loss of CAT activity in response to afferent denervation.

Deafferentation can be experimentally induced by ZnSO$_4$ lavage of the nasal epithelium, which destroys olfactory receptor neurons (Harding et al., Brain Res., 140:271–285, 1978: Cancalon, Tissue Cell, 14:717–733, 1982). Under certain conditions, ZnSO$_4$-induced deafferentation does not result in permanent loss of olfactory epithelial neurons (Harding et al., Brain Res., 132:11–28, 1977; Cancalon, supra) such that regeneration of the olfactory neurons occurs over time. An 8 d time point was chosen in our experiments because previous work has shown that at 8 d, no regeneration should have ensued. Transgenic animals were deafferented by a bilateral intranasal irrigation with 0.17M ZnSO$_4$. Eight days later, one OB from each animal was assayed for CAT expression, and endogenous dopamine was quantitated in the other bulb. Previous work had shown that ZnSO$_4$ deafferentation reduces dopamine to 15–30% of control levels (Nadi et al., Brain Res., 213:365–377, 1981; Kawano and Margolis, supra).

Control saline-treated animals had CAT expression comparable to untreated transgenic mice, establishing that intranasal irrigation had no effect on CAT activity (Table 2). Dopamine levels in these animals were also comparable to levels in saline-treated wild-type littermates of the transgenic animals. In contrast, the dopamine levels in the ZnSO4-treated transgenic mice were about 30% of those from the saline-treated animals after 8 d, demonstrating that the deafferentation was successful. CAT activity in the same animals dropped to 41% of levels in control animals (saline-treated and untreated transgenic animals), similar to the reported decrease in TH enzyme activity assayed 7 d after lavage (Nadi et al., supra). Therefore, the reduction in CAT expression in these animals shows that the transgene is regulated by afferent input, arguing that CAT expression is cell specific, and the TH DNA elements in the transgene are capable of mediating the transsynaptic effect.

Discussion 4.8 kb of 5' TH sequences for tissue specific expression

The 4.8 kb of upstream TH sequence used in these studies targets expression of CAT exclusively to tissues containing TH-expressing cells; we observed expression in the adrenal, scg, and regions of the brain that contain TH-positive neurons. CAT activity was undetectable in all of the other tissues assayed including liver, heart, spleen, and kidney. Areas of the brain that are innervated by TH neurons, but do not contain TH cell bodies, contained very low levels of CAT activity, perhaps due to small amounts of transported CAT protein.

The total amount of CAT per region, calculated from the amount of protein recovered from each region and the specific activities in FIG. 2, roughly paralleled the number of TH neurons in each area. Although exact counts of TH neurons are not available in the mouse, if mice and rats have the same proportion of TH neurons in various regions, the OB has the largest number of TH neurons (150,000 per bulb in the rat) (McLean and Shipley, supra) and by far the greatest CAT activity. The next largest group of TH neurons, the SN-VTA (Bjorklund and Lindvail, supra), has about one-quarter the number of TH neurons in the OB and about one-quarter as much CAT. Likewise, the pons-medulla has one-quarter as many cells as the SN-VTA and proportionately less CAT. The hypothalamus has the fewest TH neurons but has disproportionately high CAT activity, with levels between that of the SN-VTA and the pons-medulla. Part of this activity may be due to axonally transported CAT, since the hypothalamus is heavily innervated by TH-positive neurons. Nevertheless, CAT expression in dissected brain regions is specific to areas bearing TH cell bodies, and largely reflects the number of TH cells in each region.

When compared to endogenous TH activity in a given region, CAT expression was higher in the CNS (OB and brain) than in the PNS (adrenal or scg). This suggests that the TH regulatory sequences used in this study preferentially target expression to the CNS, although CAT activity is clearly present in the adrenal and scg. These data are consistent with a recent study (Kaneda et al., 1001, supra) in which the entire human TH gene (including 2.5 kb of upstream TH sequences, the entire coding region with introns, and 0.5 kb downstream sequences) directed a 10-fold lower expression of the human TH transgene in the adrenal as compared to the brain. Although our construct includes an extra 2.3 kb of 5' DNA (from −2.8 to −4.8 kb), there is still a 20-50-fold higher CAT expression in the CNS compared to adrenal. Therefore, elements required for full PNS expression may still be lacking in the −4.8 construct. Since our study measured TH and CAT enzyme activities, the observed disparity could reflect the post-transcriptional events, although the study by Kaneda et al. demonstrated a similar disparity in the RNA expression.

Our results differ from previous studies (Kaneda et al., supra; Morgan and Sharp, supra.; Suri and Chikaraishi, Embo. J., 10:289–296, 1991) by demonstrating CAT expression in the OB and in the sympathetic ganglia (scg). Furthermore, our data on dissected brain regions reflects accurate expression of CAT in all the appropriate brain regions; in contrast, previous studies using up to 3.5 kb of upstream sequences from the mouse TH gene and the entire coding region including introns as well as 0.5 kb of downstream region from the human gene demonstrated ectopic expression in the brain. Although some regions were correctly targeted, inappropriate reporter expression occurred in a variety of CNS loci. Taken together, these data imply that elements between −3.5 and −4.8 kb may be important for restricting ectopic CNS expression. Using 2.8 kb of the 5' flanking region of the rat TH gene resulted in a similar mixed pattern of appropriate and ectopic expression (Suri and Chikaraishi, supra, the disclosure of which is incorporated by reference herein and infra, Example 5). This indicates that at least in the rat gene, elements that lie between −2.8 and −4.8 kb are important for allowing full expression in all TH-positive areas, and suppressing ectopic expression. These data imply that multiple elements spread over as much as 4.8 kb of flanking DNA may mediate activation and repression to generate the final pattern of TH expression. Although our data implicates a long 5' flanking region for correct cell specificity, it does suggest that coding, intronic, and 3' flanking sequences are not necessary.

CAT expression in the OB parallels endogenous TH expression both in response to transsynaptic stimulation, and during development We show that 4.8 kb of TH flanking DNA directed accurate developmental regulation of CAT in the OB. The postnatal rise in endogenous TH activity was directly paralleled by postnatal increase in CAT expression. Both activities increased until 3 weeks after birth. This plateau at 3 weeks is in contrast with results obtained by McLean and Shipley (supra) in the rat, using immunohistochemical methods in which they demonstrated that the number of TH-immunoreactive cells increase linearly until 2 months after birth. However, a more prolonged time course for the development of TH in the rat as compared to the mouse has been demonstrated in the scg (Black et al., Brain Res., 75:133–144, 1974); perhaps the same occurs in the OB. Nevertheless, in the mouse OB, the CAT reporter activity reflected endogenous TH activity.

Unlike most other TH cell groups, OB neurons need to complete their migration and receive their afferent innervation before they express TH, implying that developmental TH expression is a manifestation of transsynaptic regulation. However, it has recently been suggested that the presence of intact afferent connections may not be sufficient for maintaining TH in the OB; rather, the maintenance of TH requires input electrical activity from afferent fibers. If the OB is allowed to develop normally, but odorant access is occluded by naris cauterization, there is a decrease in dopamine content (Brunjes et al., Dev. Brain Res., 22:1–6, 1985), TH immunoreactivity, TH enzyme activity (Kosaka et al., Brain Res., 413:197–203, 1987), and TH message (Stone et al., Mol. Brain Res., 8:291–300, 1990), although the result is less dramatic than that resulting from chemical or surgical deafferentation This indicates that development of TH expression in the OB is activity dependent. Thus, our construct contains sequences to mediate the developmental induction of TH, which occurs in an activity-dependent manner.

To demonstrate directly that CAT expression is transsynaptically regulated in a manner similar to the endogenous TH in the OB, we chemically deafferented the OB. $ZnSO_4$-induced necrosis of the olfactory epithelial neurons removes afferent innervation to the dopaminergic neurons of the OB. This results in a progressive loss of TH expression such that 8 d after $ZnSO_4$ treatment TH activity is about 40% of normal levels, which is also reflected in dopamine levels (Nadi et al., supra; present results).

In $ZnSO_4$-treated transgenic mice, CAT levels dropped to about 40% to those of saline-treated controls, and dopamine levels fell to about 30% of control levels after 8 d, which are comparable to levels found by others for TH and dopamine, respectively (Nadi et al., supra; Kawano and Margolis, supra).

In conclusion, in this experiment, we have generated a line of transgenic mice that express a CAT reporter driven by 4.8 kb of 5' TH sequences, in a manner reflecting endogenous TH expression in all tissues tested, including discrete brain regions. Furthermore, in the OB, there is accurate transsynaptic and developmental expression of CAT, suggesting that 4.8 kb is insufficient for mediating these events.

EXAMPLE 2

HGH Used With the 4.8 kb Regulatory Region

Human growth hormone: To assess in which cell type the targeted transgene is expressed in transgenic animal, a target gene that can be detected histologically is advantageous, since its presence can be localized to individual cells. In an organ such as the brain, which is composed of many different types of neurons, the ability to localize transgene presence to individual cells is crucial to assessing if the transgene is correctly targeted Therefore, the human growth hormone gene was inserted into the 4.8THO plasmid. Since commercially available antibodies (from Amel) to human growth hormone can be used to detect growth hormone in tissue sections, it serves as a good histologically-detectable transgene. In addition, it can be quantitated by radioimmune assay using commercially available kits from Allegro or Hybritech in tissue extracts.

In addition to assessing the specificity of transgene expression, the resulting animals could be used to study the effect of growth hormone expression in the catecholaminergic neurons of the CNS and in the chromaffin cells of the adrenal medulla. One potential use would be to create a new model for growth hormone deficiency by expressing human growth hormone in the hypothalamus of transgenic mice.

Method: The 4.8 TH upstream region was excised from 4.8THO with HindIII and Sal I and cloned into the HindIII and Sal I sites of the pOGH described by Selden et al. (Mol. Cell. Biol., 6:3173–3179, 1986, the disclosure of which is incorporated by reference herein). The resulting construct, termed 4.8 TH-GH (FIG. 4B) contained TH sequences from −4.8 kb to +10 bp followed by unique Nru I, Sma I and Sal I site remaining from the THO linker followed by the human growth hormone sequences including splicing a polyadenylation sites and pUC12 plasmid sequences from pOGH. A linear fragment devoid of plasmid sequences was isolated after restriction digestion with Eco RI, purified as described above in Example 1, and injected into fertilized mouse B6D2 mouse eggs as described in Example 5. TH-GH mice were identified by tail DNA dot blots.

Mice that had previously been identified as transgenic by dot-blot analysis were anaesthetized with an intraperitoneal injection of Avertin, placed on a stereotaxic instrument modified for mice and unilaterally infused with 10 μg of colchicine (Sigma Chemical Co., St. Louis, Mo.) in 5 μl of 0.9% NaCl at the following co-ordinates with respect to Bregman:AP=0.0, LM=1.2 and V=3.4. 24 hours later, animals were anaesthetized with an intraperitoneal injection Nembutal and perfused with 4% paraformaldehyde in 0.1M phosphate buffer containing 5% sucrose. Brains were further postfixed for 4 hours and transferred to 10% sucrose. They were transferred to 20% sucrose the following morning and subsequently flash-frozen in dry-ice and stored at −70° C. until sectioned. 30 μM coronal sections were cut on a sliding microtome and stored until further use in 0.5M Tris-saline with 1% $NaN_3$ at 4° C. Immunohistochemistry was performed on these floating sections using as primary antibody a rabbit anti-hGH primary antibody (1:1000) kindly provided by Dr. Savatore Raiti and NIH national hormone and pituitary program, or a rabbit anti-TH (dilution of 1:480, Eugene-tech), using a peroxidase-anti-peroxidase (PAP, method of Sternberger, L.A., 1979, in "Immunohistochemistry", Wiley, N.Y.) double-bridge method. After a buffer rinse with 0.5 M Tris-saline (pH 7.6), sections were treated with 10% MeOH/3% $H_2O_2$ for 5 mins., and 1:30 normal goat serum (NGS) for 30 mins blocking antibody). Primary antibody incubation was carried out at 4° C. for 3 days, secondary antibody (commercially available goat anti-rabbit antibody) was used at 1:100 for 30 mins. at room temperature followed by PAP (1:100) incubations for 30 mins. at room temperature. The incubations with the secondary antibody and the PAP was repeated a second time under the same conditions. Primary and secondary antibodies and the PAP also contained 1% NGS and 1% normal mouse serum (NMS). Buffer rinses in 0.5M Tris-saline were carried out between steps. Sections were developed in diaminobenzidine (DAB)-$H_2O_2$ for 2–6 mins. Stained sections were mounted onto gelatin-coated slides, allowed to dry overnight, dehydrated, and mounted.

Results: FIG. 11 shows examples of the expression of growth hormone in the brain: telencephalon (olfactory bulb), pons-medulla (locus coerules), midbrain (ventral tegmental area) and diencephalon (hypothalamus) and adrenal medulla of transgenic mice bearing the growth hormone transgene under the control of the TH regulatory region. To prevent transport of growth hormone into axon terminals, the animals were injected intraventricularly with colchicine (as described in the methods, supra). As shown, growth hormone is expressed in the same cell populations as the endogenous TH gene. These and other similar data show that the GH target gene was expressed in all the correct TH-expressing neurons in the mouse CNS, with no evidence of inappropriate or ectopic expression in the CNS or in any somatic tissue tested.

Uses: The growth hormone target gene allowed the assessment of the specificity of the 4.8 TH regulatory region at the single cell level. Because it is in the correct CNS TH cells, the expression of growth hormone is likely to be regulated similarly to the endogenous TH gene and could be used to assess stimuli that regulate endogenous TH.

Figure 12:
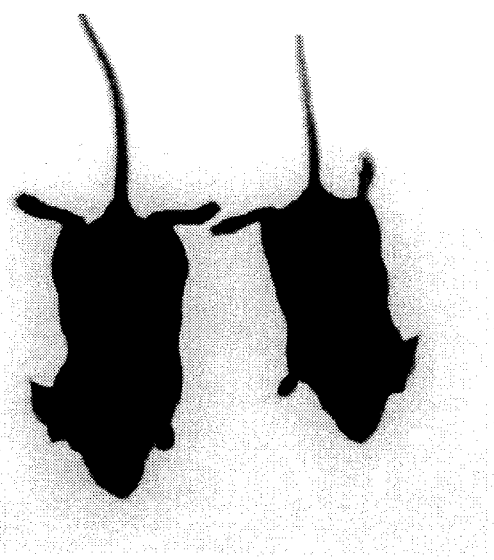
FIG. 12 illustrates the smaller size of the HGH transgenic mouse compared to its non-transgenic littermate at the time of weaning.

The transgenic growth hormone mice could also be used as a new genetic model for isolated growth hormone deficiency. FIG. 12 shows that the TH-GH mice are dwarfs. Heterozygotes, on average, are 20–30% smaller at weaning than their wild type siblings. The dwarfism is likely to be due to the hypothalamic expression of GH from TH-expressing cells that suppresses growth hormone releasing hormone (GRH) and induces expression of somatostatin in the mouse hypothalamus. Reduced GRH and increased somatostatin suppress production of the endogenous mouse growth hormone from the pituitary. The result is a reduction in the level of circulating mouse growth hormone that, in turn, prevents normal somatic growth in the transgenic mice. Measurements have demonstrated that the level of circulating mouse growth hormone are reduced about 50% in TH-GH mice consistent with this model.

EXAMPLE 3

Expression of a Toxic Gene Using 5' Flanking Sequence

Toxin target genes: By using a toxic gene as the target gene of choice in transgenic animals, one could kill those cells that normally express TH in the animal by virtue of the expression of a toxic gene in those cells. These animals could be used as new genetic models for neurological diseases in which the TH-expressing cells are compromised, such as Parkinson's Disease or dysautonomia (a dysfunction of the sympathetic nervous system).

Method: For example, the diptheria toxin A chain which is lethal to almost all mammalian cells could be used as a target gene for the 4.8 TH region. A diptheria toxin A chain gene could be inserted into the linker region of 4.8THO using the appropriate restriction enzymes sites to excise the toxin gene from a plasmid and ligate the gene into the TH plasmid. Suitable forms of the toxin genes have been described (Maxwell et al., supra, the disclosure of which is incorporated by reference herein), which could be used for this purpose. For example, diptheria toxin A chain could be excised from the clone described by Maxwell et al., supra, with Bam HI and Eco RI. A linker which restores the ATG for translational initiation (which would recreate the Bam HI site preceded by AT dincucleotide) and includes an internal restriction site for Sal I followed by sequences that would reconstruct the Eco RI site could be ligated onto the diptheria gene fragment. After digestion with Sal I, the fragment could be cloned into the Sal I site of 4.8THO, creating a plasmid (4.8 TH-DT) bearing the diptheria toxin gene under the transcriptional control of the rat TH regulatory region. The DNA fragment used for injection into transgenic mice could be prepared after digestion of the TH-DT plasmid with Eco RI. The effect of the toxin could be assayed by the loss of TH antibody staining in the resulting animals.

EXAMPLE 4

Neurotrophic Growth Factors as Targets

Many models of neurodegenerative disease are based on the hypothesis that lack of endogenous growth or survival factors result in deficits. Several animal models (such as surgical, chemical or genetically induced neuronal death) are in use (see Zigmond and Stricker, International Review of Neurobiology, 31:179, 1989 for animal models of Parkinson's Disease, the disclosure of which is incorporated by reference herein). Using the 4.8 TH region, one could target the expression of various cloned neurotrophic growth factors such as nerve growth factor, brain-derived neurotrophic growth factor, or neurotrophin-3 to catecholaminergic neurons and adrenal chromaffin cells. One could test whether expression of a given growth factor in TH expression cells prevented the neurodegeneration induced in transgenic mice.

EXAMPLE 5

Immortalization of Catecholaminergic Neuronal Cells

In this example, we have used the upstream elements of the rat tyrosine hydroxylase gene to drive the SV40 T antigen oncogene to generate tumors in the TH-producing cells of the central and peripheral nervous systems. TH is the first and rate limiting enzyme in the catecholamine biosynthetic pathway. It converts L-tyrosine into dihydroxyphenylalanine (L-DOPA) from which are sequentially synthesized dopamine (DA), norapinephrine (NE) and epinephrine (E) such that all catecholamine-producing cells express TH. The 5' upstream regulatory region of the TH gene has been well studied (Lewis et al., Proc. Natl. Acad. Sci. USA, 84:3550–3554, 1987, the disclosure of which is incorporated by reference herein; Cambi et al., supra; Gizang-Ginsberg and Ziff, Genes Dev., 4:477–491, 1990; Fader and Lewis, Mol. Brain Res., 8:25–29, 1990; Fung et al., supra, the disclosure of which is incorporated by reference herein), and elements necessary for cell-specific expression in cultured cells (Fung et al., supra) and in transgenic mice (Examples 1, 2 supra) have been defined. The expression of TH in the nervous system has been well established. It has a specific tissue distribution the CNS in discrete nuclei mainly in the olfactory bulb, midbrain and brainstem regions (Bjorklund and Lindvail, supra). In the PNS it is most abundant in the chromaffin cells of the adrenal medulla and in sympathetic ganglia (Rothman et al., Proc. Natl. Acad. Sci. USA, 77:6221–6225, 1980). In the rodent CNS (excluding the olfactory bulb), the total number of TH-producing cells is less than 50,000, scattered across a number of sites, which makes the isolation of pure populations of TH-positive cells very difficult. Since TH in the CNS is expressed only in post-mitotic neurons (Specht et al., supra), immortalization of TH-expressing neurons using retroviruses is unlikely.

SV40 T antigen (Tag) has been shown to induce tumors in a wide variety of tissues. Though other oncogenes such as c-myc and H-ras have been demonstrated to induce tumors, they are relatively restricted in the types of tissues that they can transform (Davis et al., Accomplishments in Cancer Research ed., pp. 110–118, 1987; Sinn et al., Cell, 49:465–475, 1987, the disclosure of which is incorporated by reference herein). SV40 Tag, on the other hand, has been successful in inducing tumors in many cell types and, in particular, has been used to generate tumors in endocrine and neural tissues. For example, endocrine pancreatic tumors have been induced when Tag was under the control of promoters for insulin (Hanahan, Nature, 315:115–122, 1985), glucagon (Efrat et al., Neuron, 1:605–613, 1988) and vasoactive intestinal peptide (VIP; Murphy et al., Am. J. Pathol., 129:552–566, 1987); anterior pituitary tumors were produced with the promoters for VIP (Murphy et al., supra) and glycoprotein hormone e-subunit (Windle et al., Mol. Endocrinol., 4:597–603, 1990); retinal and adrenal gland tumors were obtained with the phenylethanolamine N-methyl transferase (PNMT) promoter (Baetge et al., Proc. Natl. Acad. Sci., USA, 85:3648–3652, 1988) and hypothalamic tumors have been generated with the GnRH promoter (Mellon et al., supra).

We disclose here the immortalization of cells from the brain and adrenal glands of transgenic mice bearing SV40 Tag under the control of 773 bp of the upstream regulatory region of the rat TH gene. We have established three cell lines which possess a neuronal phenotype, indicated by the presence of neurofilament proteins and the absence of glial fibrillary acidic protein. The lines are strongly catecholaminergic, synthesizing high levels of TH enzyme and producing both DA and NE. They also contain synaptophysin, a protein specific to small synaptic vesicles in neurons and related small vesicles in neuro endocrine cells (Navone et al., J. Cell Biol., 103:2511–2527, 1986; Johnston et al., EMBO, 8:2863–2872, 1989).

Materials and Methods

Plasmid construction: The plasmid 4.8THO (FIG. 4A) was created from 4.8THCAT by replacing the region between the −19 (Nar I site) and +2562 (Nar I site, which is the unique Nar I site in pUC vectors at position +235, Yanisch-Perron et al., supra) with a synthetic linker sequence containing TH sequences from −18 to +10 followed by cloning sites for the restriction enzymes SmaI, Nru I and Sal I. The sequence of the linker is 5' CGCCTGC-CTGGCGAGGGCTGTGGAGACACCCGGGTGG 3' (SEQ. ID NO. 1). Two copies of the linker were inserted such that the 4.8THO plasmid contains rat TH sequences between −4.8 kb to +10 bp, followed by two copies of the linker sequence, which end by reconstructing the unique Nar I site in the puC vector. The remainder of the plasmid consists of pUC vector sequences from the Nar I site to the polylinker region and extending into the pUC polylinker region with Hind III and Eco RV and Eco RI sites. The Eco RI starts the rat TH genomic DNA at about −4.8 kb. The plasmid retains an ampicillin resistance gene and a Col El origin or replication. A 2.7 kb StuI-BamH1 fragment from wild type SV40 DNA (Fiers et al., Nature, 273:113–120, 1978, the disclosure of which is incorporated by reference herein) was blunt ended and inserted into the unique SmaI site of 4.8THO to generate 4.8THTag. Digestion with XhoI and Sal I yielded a linear piece of DNA containing the complete coding sequence for Tag (2.7 kb) under the control of −773 bp of TH. The DNA was purified from agarose gels by the sodium perchlorate method (Chen and Thomas, Anals. Biochem., 101:339–341, 1980, the disclosure of which is incorporated by reference herein) and resuspended at a concentration of 5ng/µl for injections.

Transgenic mice: The procedures were done essentially as described by Hogan et al. (supra), the disclosure of which is incorporated by reference herein. DNA was injected into the male pro-nucleus of recently fertilized eggs from B6/D2 F1 donor mice (Taconic Labs). Following an overnight incubation at 37°, the 2-cell embryos were implanted into the oviducts of pseudo-pregnant CD-1 females (Charles River Labs). Pups bearing the transgenes were identified by a tail blot in which DNA from a tail segment was isolated, bound to nitrocellulose filters and probed with a radiolabelled DNA fragment corresponding to Tag. Pups were screened for the presence of an un-rearranged transgene by Southern analysis (Maniatis et al., *Molecular Cloning: A Laboratory Manual*, Cold Spring Harbor Labs., 1982, the disclosure of which is incorporated by reference herein).

Cell culture: Tumors were removed under sterile conditions and cut into small pieces. These were mechanically triturated in RPMI 1640 media containing 0.018% Type I collagenase (Worthington Biochemical Corp.) with a 0.2% bovine serum albumin (Sigma) ad placed at 37° for 20–25 min. The reaction was stopped by the addition of serum containing media, and the cells were triturated again and pelleted. They were then plated onto tissue culture plastic and grown in media containing RPMI 1640 supplemented with 8% horse serum, 4% fetal bovine serum, 1% Pennicillin-Streptomycin (stocks of 10,000 U/ml Penn. G and 10,000 mcg/ml Strep. sulphate; Irvine Scientific) and 20 units/ml Nystatin (GIBCO). The mixed primary cultures were passaged once a week using 0.12% Trypsin without EDTA (Irvine Scientific). Even in primary cultures, few glial or fibroblastic cells were evident. For cloning purposes, cells were grown at a low density and glass cylinders were used to isolate individual colonies which were triturated to clumps of 1–10 cells in the presence of 0.12% Trypsin (without EDTA), and replated at cloning densities. This procedure was performed thrice.

PATH.1 was grown on dishes coated with poly-L-lysine (Sigma) at a concentration of 100 µg/ml to improve attachment. This procedure did not affect the properties of the cell line.

Immunochemistry: Tissues and tumors were immersed in Bouin's fixative (75 ml saturated picric acid, 25 ml 37% formaldehyde, 5 ml glacial acetic acid) for 4 hrs. to overnight depending on tissue thickness, after which time they were treated as required for cyrostat or paraffin sectioning. Cyrostat (9–12 µm) and paraffin (6 µm) sections were usually placed on 0.01% poly-L-lysine coated slides. Cell lines were grown on poly-L-lysine coated glass cover-slips placed in a 24-well plate, and were fixed by a 15 min. exposure to Bouin's fixative.

0.3% Triton X-100 in potassium phosphate buffered saline (T/KPBS) was used for permeabilization and was present until the enzymatic reaction was performed in the last step of the procedure. 1% hydrogen peroxide in absolute methanol was added to the sections or cells for 20 min. to reduce background due to endogenous peroxidase activity. For Tag detection, tissue sections were treated with 0.003% bacterial protease XXIV (Sigma) in T/KPBS for 15 min. This treatment partially digested the cellular proteins, including Tag, thereby better exposing the antigens. Since the proteolytic treatment tended to increase background staining, these sections were routinely blocked with avidin followed by biotin (Blocking kit, Vector Labs.). These solutions were used undiluted and as provided by the supplier. All sections and cells were incubated in 2% normal goat serum (Vector Labs.) and 1% Carnation non-fat dry milk in T/KPBS for 30 min. to block non-specific binding prior to addition of primary antibody.

Primary antibody incubations were at 4° for 1–3 days depending on the antigen. TH antiserum (Eugene Tech.) was a rabbit polyclonal antiserum against bovine TH. It was used at a dilution of 1:250 or 1:500, depending on the batch. Tag antiserum (rabbit polyclonal) from Dr. D. Hanahan (UCSF), and was used at a 1:5000 dilution for tissue sections and at a 1:10000 dilution for cells (Hanahan et al., 1985, supra, the disclosure of which is incorporated by reference herein). Anti-synaptophysin was a rabbit polyclonal against the rat antigen from Dr. J. Wang (Tufts U. Med. School) and was used at a dilution of 1:200. Antibodies against the medium chain of NF and GFAP were from Dr. V. Lee (U. Penn.). Anti-N, a mouse monoclonal, was used at a dilution of 1:10, and anti-GFAP, a rat monoclonal, at a dilution of 1:100. The antibodies can be prepared by standard immunological techniques described in Harlow and Lane, *Antibodies: A Laboratory Manual*, Cold Spring Labs., 1988, the disclosure of which is incorporated by reference herein. The buffer for dilutions contained 1% Carnation non-fat dry milk in T/KPBS with 0.02% sodium azide. Sections were covered with glass cover-slips to prevent drying. Biotinylated secondary antibodies (goat anti-rabbit, horse anti-mouse, and goat anti-rat) were obtained from Vector Labs and used at a dilution of 1:200 in T/KPBS with 1% Carnation milk for 2 hrs. at room temperature. Antibody reactions were visualized with an enzymatic assay utilizing the peroxidase enzyme linked to avidin (ABC kit, Vector Labs.). Section and cells were incubated in the ABC mix for 1 hr. at room temperature. Diamino-benzidine (at 40 mg/100 ml in Tris buffered saline or TBS, pH 7.4) and hydrogen peroxide (at 0.003%) acted as substrates and NiCl (at 0.04%) as an enhancer for the reaction, which was allowed to proceed until the blue/black color was visible, but not more than 20 min. All sections and cells were dehydrated in ethanol and xylene, and permanently mounted with Permount (Fisher Sci.).

TH enzyme activity: (Modified from Rittenhouse et al., supra, the disclosure of which is incorporated by reference herein). Cells were grown to 70% confluency on 65 mm plates. They were rinsed twice with cold phosphate buffered saline (PBS), scraped off and pelleted at 10K rpm for 10 min. The pellet was homogenized in 150 µl of a buffer containing 0.1% Triton X-100 in 5 mM Tris pH 6.0 and re-centrifuged. The supernatant (10 µl aliquots) was assayed in duplicate at 37° C. for 6 min. in a reaction mix consisting of 200 mM $KHPO_4$ pH 6.0, 3.2 mM 6-methyl-5,6,7,8 tetrahydropterin, 80 µM L-tyrosine, 300 µM brocresine, 40 mM β-mercaptoethanol and $2\times10^5$ units/ml catalase. 25 pmoles of epinephrine in 0.1 mM EDTA and 0.5M Tris pH 8.6 were used to stop the reaction. Catecholamines were allowed to bind to acid-washed alumina for 15 min. with constant shaking. The alumina was then pelleted and washed twice with 0.1M $NaHSO_3$ in 0.5M Tris pH 8.6. The bound catechols were eluted with 0.1M $H_3PO_4$, 0.1 mM EDTA and quantitated by HPLC.

DBH enzyme activity: (Modified from Sperk et al., J. Neurochem., 35:972–976, 1980, the disclosure of which is incorporated by reference herein). Cells were grown and pelleted as above. They were sonicated after resuspension in cold 50 mM sodium acetate pH 6.0 with 1% Triton X-100. After one freeze-thaw cycle, they were centrifuged at 12K rpm for 10 min. 10 µg of protein was added to 100 µl of 1%

Concanavalin A sepharose 4B beads in 50 mM sodium acetate pH 5.5. DBH was allowed to adsorb to the beads for 15 min. at 4° C., and the beads were pelleted at 12K rpm for 3 min. They were washed thrice with ice water and resuspended in 200 µl of 50mM sodium acetate pH 5.5. The enzymatic assay was performed at 37° C. for 30 min. using 100 µl of DBH-bound beads in a final reaction volume of 200 µl. The reaction mix contained 3 mM dopamine, 4 mM ascorbic acid, 40 mM fumarate, 0.6 mM pargyline, 700U catalase, 3 µM copper sulphate, 50 mM sodium acetate pH 5.5. The reaction was stopped by chilling on ice and with the addition of 0.5 volumes 2M Tris pH 8.6. The catecholamines were extracted with alumina as described for the TH assay and detected by HPLC.

HPLC: A C-18 reverse phase column (Beckman Co.) was used in combination with an electrochemical detector (Waters). The mobile phase contained 7.5% methanol, 50 mM $NaH_2PO_4$ pH 3.6, 0.387 mM sodium octyl sulphate and 0.1 mM EDTA.

Northern analysis: Cells were grown on 150 mm plates. Poly-$A^+$ RNA was prepared using the Fast Track mRNA isolation kit (Invitrogen). Northerns were performed as described (Maniatis et al., supra) using 2 µg of poly-$A^+$ RNA per lane of a 1% formaldehyde agarose gel. Molecular weight markers ranging in size from 0.24–9.49 kb were purchased from BRL. After electrophoresis the gel was immersed in 0.05N NaOH for 20 min., rinsed in DEPC-treated $H_2O$ and equilibrated in 1x SSC buffer (0.15M NaCl, 15 mM sodium citrate pH 7.0). RNA was transferred to a Genescreen membrane by passive capillary flow for at least 20 hrs, and cross-linked to the membrane by exposure to 1600 Joules of UV radiation. The membrane was pre-hybridized for at least 5 hours at 42° C. in a buffer containing 50% formamide, 5x SSC, 0.1% SDS, 0.1% sodium pyrophosphate, 120 µg/ml salmon sperm DNA, 10x Denhardt's reagent and 10% dextran sulphate. Hybridization was done overnight under similar conditions in the presence of a radioactive probe. The membrane was washed at 65° C. under stringent conditions and exposed to Kodak XOMat film for autoradiography.

Sources of DNA for making radiolabelled probes were as follows: TH plasmid RR1.2 (Cambi et al., supra), NF plasmid (gift of Dr. N. Cowan, NYU) and PNMT plasmid (gift of Dr. E. Weisberg, U. of Pittsburgh). DNA probes with an average specific activity of 180 million cpm//µg template were made by random priming of the intact TH and PNMT plasmids (Maniatis et al., supra). NF RNA probe of a similar specific activity was made according to standard protocols.

Determination of total catecholamines: Cells were grown on 65 mm plates, washed twice with ice cold PBS and scraped off mechanically. The cell pellet was homogenized in 0.1N $HClO_4$ and 1 mM EDTA. After centrifugation for 10 min. at 10K rpm, the supernatant was neutralized with 0.5 volume of 2M Tris pH 8.6 and adsorbed to acid-washed alumina. Following this step, this procedure was as described for the TH enzyme assay.

Western blots: Cell pellets were resuspended in electrophoresis buffer (3% SDS, 5% glycerol, 0.064M Tris pH 6.8, 2% β-mercaptoethanol), placed in a boiling water bath for 5 min. and stored at −70° C. 100 µl of the mix (containing 67 µg total protein) was loaded per lane onto a 8% acrylamide-SDS gel. The proteins were transferred electrophoretically to an Immobilon membrane (Millipore). Non-specific binding was reduced by incubating the membrane for one hour in Tris buffered saline containing 0.1% Tween-20 (TBST) and 3% Carnation non-fat dry milk. It was then exposed to anti-synaptophysin serum at 1:500 dilution in the same buffer for 1.5 hrs. at room temperature. Following three washes in TBST buffer with 3% milk, horseradish peroxidase linked to donkey anti-rabbit antibody was added at a 1:2000 dilution for 40 min. at room temperature. The membrane was washed thrice in TBST and the bands visualized by an ECL detection system (Amersham).

Results

TH-expressing tumors in transgenic mice bearing a TH-Tag transgene: A 783 bp region of the rat TH gene, containing 773 bp of 5' upstream DNA and the first 10 bp of untranslated mRNA, was linked to the complete coding region of the wild type SV40 T antigen (Fiers et al., supra). The hybrid gene contained the mRNA initiation site at +1 from the TH gene and the translation start from the Tag sequence which also provided the natural splice sites and the polyadenylation site. The linearized construct, devoid of plasmid sequences, was injected into fertilized B6/D2 F1 ova according to Hogan et al. (supra). Seven of the twenty-two pups contained the transgene in the DNA. Southern analysis showed deletions in the transgene in two of these founders (data not shown) which were therefore discarded; the other founders contained 1–5 copies of un-rearranged TH-Tag transgene. One female founder, #17, died at 10 weeks of age during pregnancy from a massive adrenal tumor which occupied the top left quadrant of the abdominal cavity. The other four founders bred successfully but mice in three lineages were non-expressors. The remaining founder, #20, established a lineage in which the progeny consistently developed brain tumors. The age of the animals at the onset of tumors varied from 15 weeks to 8.5 months. It is likely that all animals of this lineage will develop tumors with time. In all cases the tumor-bearing mice demonstrated motor difficulties, and exhibited a hunched posture and an enlarged head. Upon sacrifice, the mice were found to have tumors on the ventral aspect of the brain, centered about the midbrain and rostral brainstem. No organ other than the brain and adrenal glands developed a tumor in any of the transgenic mice nor was there Tag staining in any of the other organs.

Sections from the tumors were either treated for immunohistochemical analysis or placed in tissue culture medium. Morphologically, both the adrenal and brain tumors resemble neuroblastomas composed of small, densely packed, undifferentiated cells with scant cytoplasm. FIG. 5 illustrates a typical staining pattern for TH and Tag proteins in adrenal and brain tumor sections. Whereas Tag can be seen in all the cells of the tumor, albeit at a variable intensity, TH is patchy in its distribution, appearing primarily in cells within a group or nodule. Interestingly, in lineage #20, expression of Tag is also observed in scattered cell nuclei in non-tumorigenic brain areas which lack TH positive cell bodies. In these areas, which include the midbrain, brainstem and specific layers in the cortex and cerebellum, stained nuclei can be seen intermingled with unstained cells (FIG. 5). This ectopic distribution of the Tag protein was also observed in the brains of siblings that had not yet developed a tumor.

With −773 bp of TH, therefore, Tag was observed in regions that were both appropriate (brain and adrenal glands) and inappropriate (non-TH producing brain cells). However, in some TH-positive regions like the olfactory bulb and superior cervical ganglia, Tag expression was never detected, suggesting that 773 bp of 5' TH information is not sufficient for a completely appropriate in vivo expression.

Derivation of immortalized cell lines: Following a 3–5 month period during which primary tumor cells were grown as mixed cultures, cell lines were isolated from both the adrenal and brain tumor cultures as described in Materials and Methods. These lines were derived by isolation of individual clumps of 1–10 cells that were plated at cloning density. The progeny of each clump were subjected to additional cycles of similar selection. After the first cycle, cells were tested for the presence of TH by immunochemical means. Approximately 50% of the adrenal lines and 12% of the brain lines contained TH. From the adrenal cultures two cell lines, PATH.1 and PATH.2 (for peripheral adrenergic tyrosine hydroxylase-expressing), have been studied extensively. They have been passaged at least once a week since February 1991. The brain culture yielded one strongly catecholaminergic cell line, CATH.a (for central adrenergic tyrosine hydroxylase-expressing), which has been cultured since April 1991. The plasmid CATH.a (FIG. 4) was created from CATH.a by replacing the region between the −19 (Nar I site) and +2562 (Nar I site, which is the unique Nar I site in pUC vectors at position +235, Yanisch-Perron et al., supra) with a synthetic linker sequence containing TH sequences from −18 to +10 followed by cloning sites for the restriction enzymes SmaI, Nru I and Sal I. A sample of CATH.a was deposited at the American Type Culture Collection on Nov. 6, 1992 under ATCC Accession No. CRL 11179. The sequence of the linker is 5' CGCCTGCCTG-GCGAGGGCTGTGGAGACACCCGGGTGG 3' (SEQ. ID NO. 1). Two copies of the linker were inserted such that the CATH.a plasmid contains rat TH sequences between −4.8 kb to +10 bp, followed by two copies of the linker sequence, which end by reconstructing the Nar I site in the puC vector at +235. The remainder of the plasmid consists of pUC vector sequences from position +235 to the polylinker region and extending into the pUC polylinker region with Hind III and Eco RV and Eco RI sites. The Eco RI starts the rat TH genomic DNA at about −4.8 kb. The plasmid retains an ampicillin resistance gene and a Col E1 origin or replication. CATH.a and PATH.2 attach well to uncoated tissue culture plastic dishes whereas PATH.1 adheres less well to standard culture plates.

Figures 6A, 6B, 6C:
FIGS. 6A–6I illustrate the morphology and immunochemical staining patterns for TH and Tag in three neuronal cell lines.
Figures 6D, 6E, 6F:
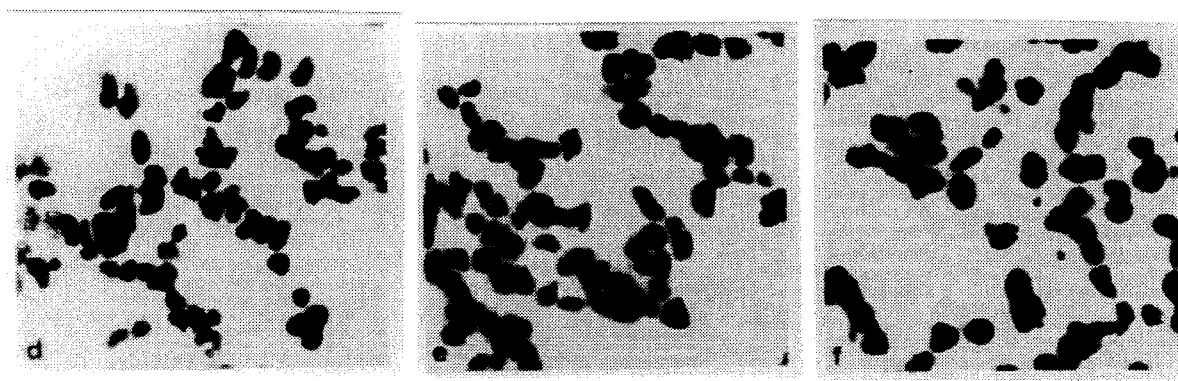
Figures 6G, 6H, 6I:
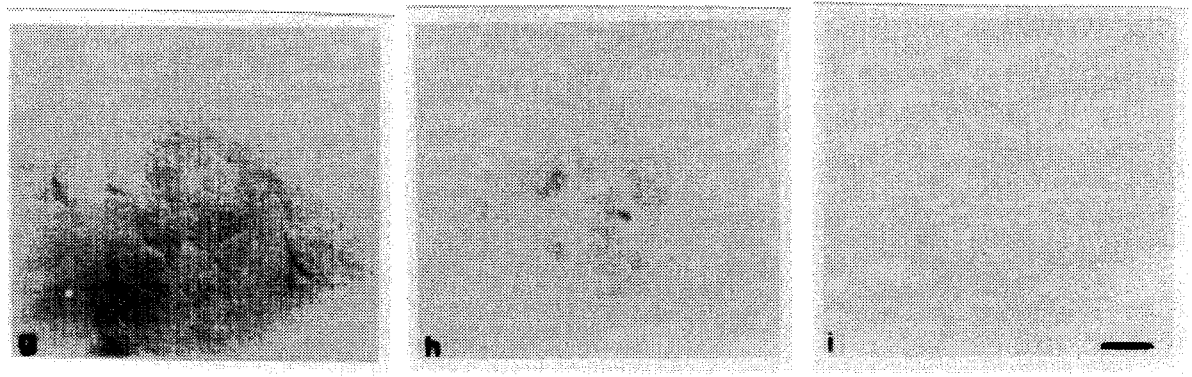

FIG. 6 shows the morphology and immunochemical staining patterns for TH and Tag in these three cell lines. All three lines grow in clumps, lack appreciable processes and appear relatively undifferentiated, with large nuclei and scant cytoplasm. They maintain this morphology when plated on poly-L-lysine, collagen, laminin or irradiated mouse 3T3 cells, or in defined media in the absence of serum. However, they stain very strongly for TH and Tag. The expected compartmentalism of TH and Tag is evident in that the TH antibody stains the cytoplasm while the Tag staining is restricted to the nucleus. While Tag staining is very robust and homogeneous, staining for TH is typically heterogeneous and of variable intensity. The same result was obtained with both a rabbit polyclonal and a mouse monoclonal antibody against TH. We have observed a similar heterogeneity in the PC8b cell line, a subclone of the PC12 cell line (Tank et al., *Catecholamine Genes*, ed., pp. 81–99, 1990). The reason for this heterogeneity is not clear. To test the possibility that TH levels are cell-cycle dependent, such that TH is only expressed in non-dividing cells, cells were grown in BuDR for 1 hr before fixation and double-stained with anti-TH and anti-BuDR antibodies. A high proportion of TH-positive cells were found to be BuDR labelled (data not shown) demonstrating expression of TH protein in cells undergoing DNA replication. Non-catecholaminergic cell lines such as NIH3T3 and ATT20 failed to stain with either TH or Tag antiserum (data not shown).

Figure 7A:
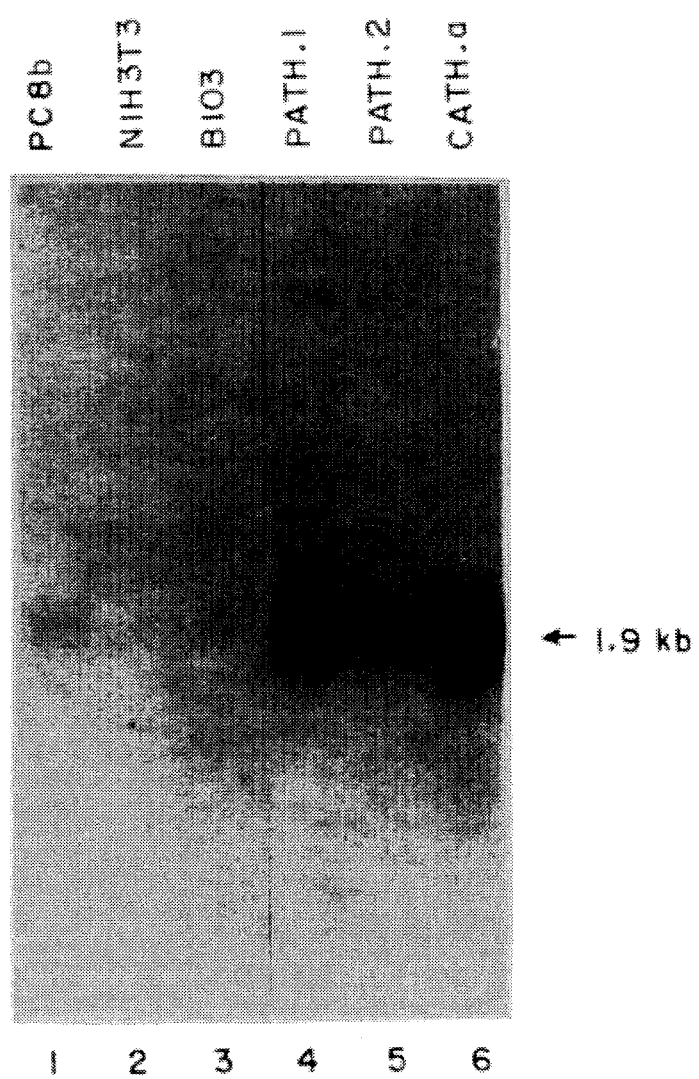
FIG. 7A illustrates that the three neuronal TH-Tag cell lines all have a strong band at 1.9 kb, the position of TH mRNA.

TH mRNA expression in cell lines: To biochemically confirm that TH is expressed in these cells, a Northern analysis was performed on poly-A$^+$ RNA. FIG. 7 (upper panel) shows that all three TH-Tag lines have a strong band at 1.9 kb, the position of TH mRNA. As expected, PC8b cells show this band although at a reduced level compared to the TH-Tag lines, and the negative cell lines NIH3T3 and B103 (a CNS neuroblastoma) do not.

The three TH-Tag cell lines therefore contain abundant TH mRNA as judged by Northern blot analysis and TH protein as judged by immunochemistry. Activities of catecholaminergic enzymes in cell lines: To determine whether the TH protein is enzymatically active, we measured TH activity in vitro. Table 3 shows that PATH.1, PATH.2 and CATH.a have TH specific activities of 776, 233 and 1129 pmoles/mg protein/min. respectively. Since the next enzyme in the catecholamine biosynthetic pathway, dopa-decarboxylase, is found in most cells, the three cell lines should be capable of synthesizing the first major catecholamine, dopamine. To determine if the cells synthesize the second catecholamine in the pathway, norepinephrine, we assayed for dopamine β-hydroxylase (DBH) which converts DA to NE. As Table 3 indicates, all three cell lines contain an active form of DBH which suggests that these cells should also produce NE if the required co-factors for TH and DBH are also present in the cells.

TABLE 3

| *Activities of catecholamine biosynthetic enzymes | | |
|---|---|---|
| | Tyrosine hydrolylase (TH) | Dopamine β-Hydrolylase (DBH) |
| CATH.a | 1129 ± 75 (4) | 160 ± 10 (6) |
| PATH.1 | 778 ± 280 (4) | 140 ± 40 (6) |
| PATH.2 | 233 ± 35 (4) | 120 ± 30 (6) |
| PC8b | 37 ± 5 (4) | 320 ± 50 (3) |
| NIH3T3 | 0 | n.d. |

*Values are in pmoles/min/mg protein ± S.D. (n); n.d.: not determined. TH enzyme activities were determined essentially as in Rittenhouse et al., supra, and DBH activities were measured according to Sperk et al., supra, both with slight modifications.

Figure 7B:
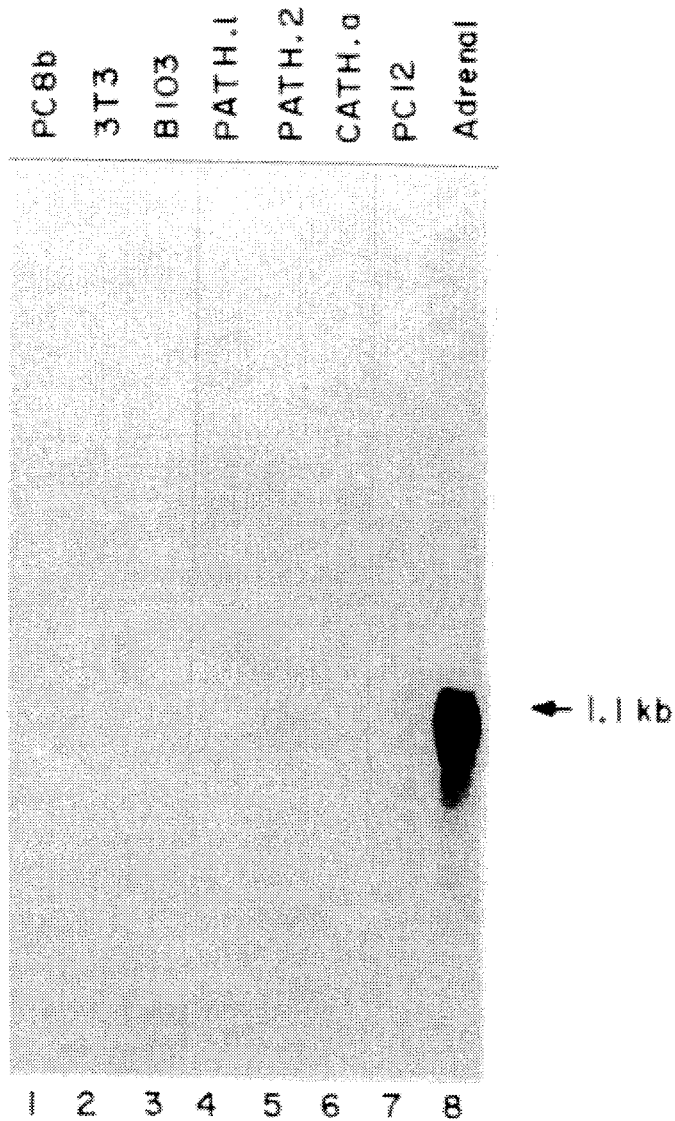
FIG. 7B illustrates that only RNA from the adrenal gland contains 1.1 kb band specific to PNMT.
Figure 8A:
FIGS. 8a–8c illustrate the immunocytochemical results with monoclonal antibodies against the medium chain of NF.
Figure 8B:
Figure 8C:
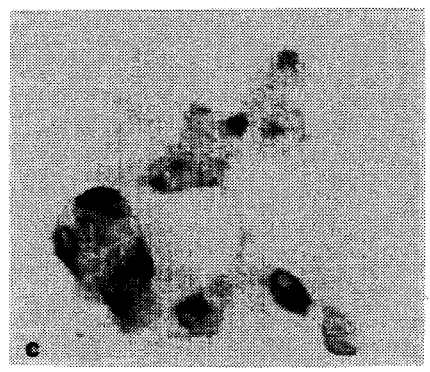
Figure 8D:
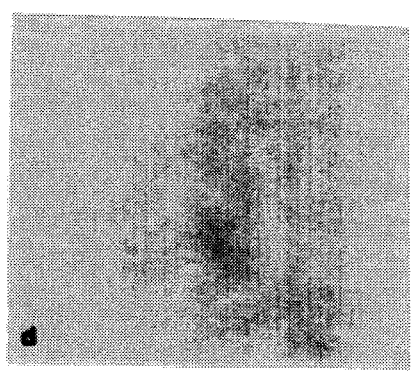
FIGS. 8d–8f illustrate that no reaction was detected when cells were stained with antibody against glial fibrillary acidic protein (GFAP) which is the intermediate filament characteristic of the CNS glial cells.
Figure 8E:
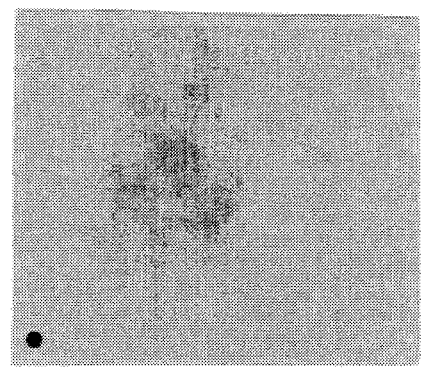
Figure 8F:
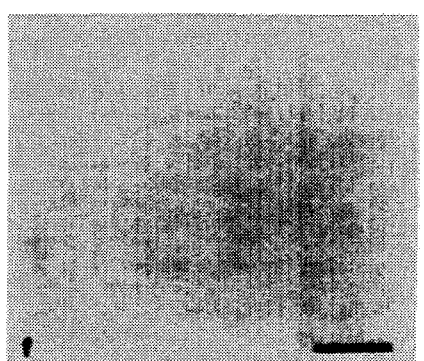

Catecholamine production in cell lines: To directly evaluate catecholamine production, DA and NE were measured in cell extracts by a reverse phase HPLC system. As with enzymatic assays, cells were plated in equal numbers and grown to similar densities before the catecholamines were extracted. High levels of both DA and NE can be detected in the cell extracts while epinephrine (E) was not detected even under conditions of high sensitivity. DA levels in all three cell-types are higher than the NE levels, the ratio of DA to NE being approximately 1.9 for PATH.1, 2.5 for PATH.2 and 2.4 for CATH.a (Table 4). Analysis of the tissue-culture medium also revealed large amounts of the two catecholamines as well as of their degradation products (data not shown), suggesting a high basal secretion and turnover. Taken together with the enzyme assays, these results suggest that all three cell lines are noradrenergic. The lack of epinephrine in these cell lines is consistent with the absence of mRNA for PNMT, the enzyme required for the conversion of NE to E. FIG. 7B (lower panel) shows that only RNA from the adrenal gland contains the 1.1 kb band specific to PNMT. None of the other cell lines, including PCl2, were found to possess this RNA species. Expression of a neuronal phenotype: The lines were assayed for the expression of neurofilaments (NF), the intermediate filaments characteristic of neurons (Lazarides, Ann. Rev. Biochem., 51:219–245, 1982, the disclosure of which is incorporated by reference herein). Neurofilaments are composed of three separate proteins of molecular weight 68 kD (light chain), 150 kD (medium chain) and 200 kD (heavy chain)(Hoffman and Lasek, J. Cell Biol., 66:351–366, 1975). FIG. 8 (a, b, c,) shows the immunocytochemical results with monoclonal antibodies against the medium chain of NF. Reaction product is clearly visible in patches near the periphery of all three cell types. The distribution of NF within cells is variable but when present it is always cytoplasmic. In contrast, when cells were stained with an antibody against glial fibrillary acidic protein (GFAP), the intermediate filament characteristic of CNS glial cells, no reaction was detected. (FIG. 8 d, e, f).

TABLE 4

| | *Catecholamine levels | |
|---|---|---|
| | Dopamine | Norepinphrine |
| | Intracellular | |
| CATH.a | 182.2 ± 12.1 (4) | 77.2 ± 2.5 (4) |
| PATH.1 | 65.7 ± 7.2 (4) | 35.0 ± 3.9 (4) |
| PATH.2 | 19.5 ± 3.4 (4) | 7.8 ± 0.8 (4) |
| PC8b | 0.8 ± 0.2 (2) | 2.7 ± 0.8 (2) |
| NIH3T3 | 0 | 0 |

*Values are in pmoles/mg cell protein ± S.D. (n)
Catecholamines were extracted by binding to acid-washed alumina and quantitated by HPLC as in Materials and Methods.

Figure 9:
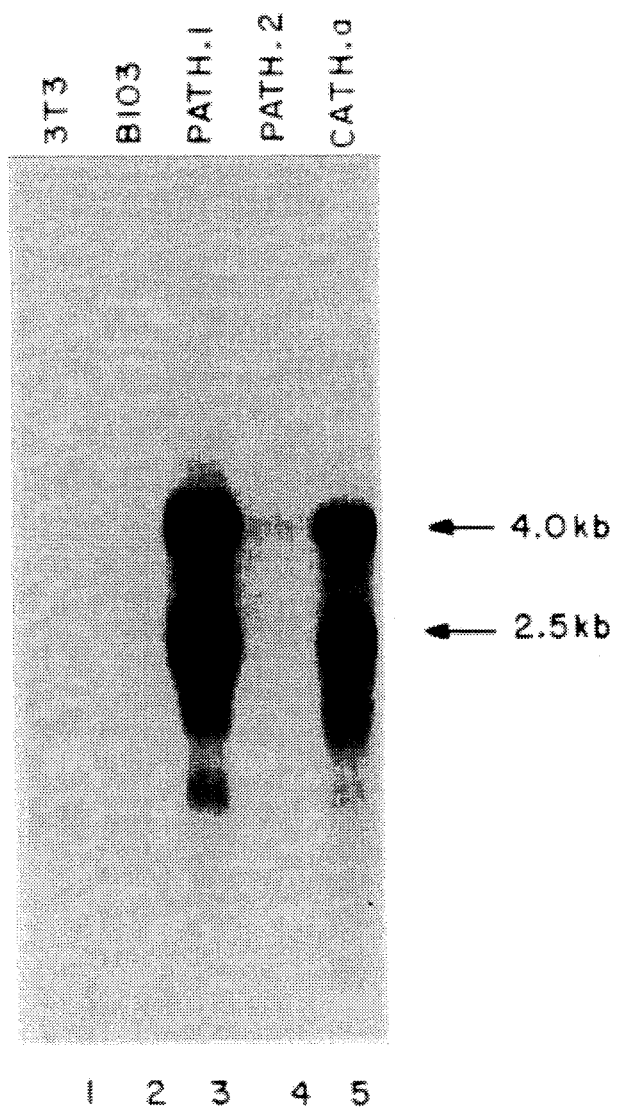
FIG. 9 illustrates that two RNA species (2.5 kb and 4.0 kb) encoding the light chain gene are readily apparent in PATH.1 and CATH.a, while PATH.2 has less of the 68 kD NF RNA.

To confirm the presence of NF using an alternate approach, mRNA from the cell lines was analyzed for the presence of the NF light chain. In FIG. 9, the two RNA species (2.5 kb and 4.0 kb) (Lewis and Cowan, J. Cell Biol., 100:843–850, 1985) encoding the light chain gene are readily apparent in PATH.1 and CATH.a, while PATH.2 has less of the 68 kD NF RNA. Nevertheless, these data in conjunction with the antibody staining demonstrates that all three lines express NFs and lack GFAP suggesting a neuronal or neuro-endocrine origin. Control cell lines, 3T3 and B103, lack NF RNA.

Figure 10A:
FIGS. 10A–10C illustrate a distinct staining pattern for all three lines from a polyclonal antibody against synaptophysin.

Expression of synaptophysin: A polyclonal antibody against synaptophysin exhibits a similar and distinct staining pattern in all three lines. The staining is largely confined to a single, intense spot near the nucleus (FIG. 10A upper panel). Control experiments showed no staining when primary antiserum was omitted or when a non-neuronal cell line, NIH3T3, was used.

Figure 10B:
Figure 10C:
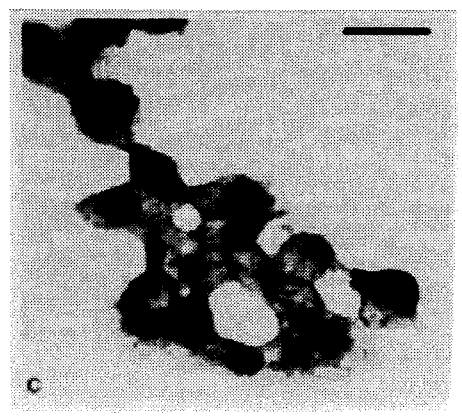
Figure 10D:
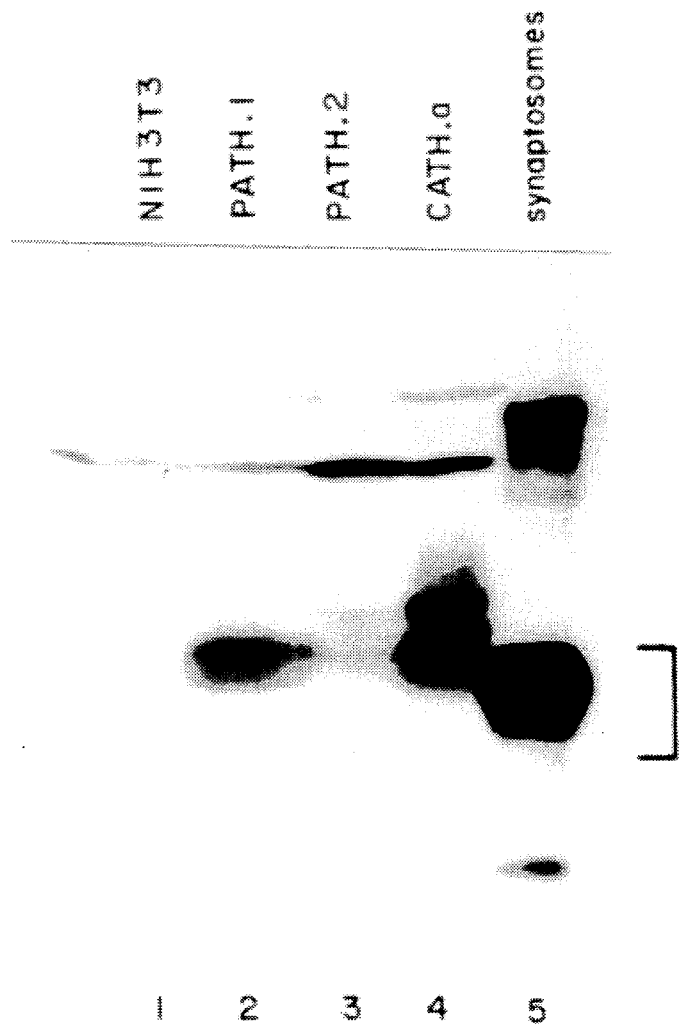
FIG. 10D illustrates that all three cell lines containing p38 proteins that can be resolved into several closely migrating species.

Synatophysin in neurons and endocrine cells is subject to differential modification by glycolsylation and sulphation, resulting in multiple forms on SDS gels (Navone et al., supra, the disclosure of which is incorporated by reference herein; Regnier-Vigoroux et al., EMBO, 10:3589–3601, 1991, the disclosure of which is incorporated by reference herein). To determine if indeed there were molecular differences in the protein between the three cell lines, a Western blot using the same polyclonal antibody was performed. As shown in FIG. 10B (lower panel), all three cell lines contain p38 proteins (indicated by a bracket) that can be resolved into several closely migrating species. PATH.1 has a high level of synaptophysin than PATH.2 and has fewer different isoforms that can be resolved on SDS gels. CATH.a has the highest concentration of p38 with several clearly distinguishable bands. In general, all three lines contain p38 proteins that migrate more slowly than those derived from a control rat brain synaptosomal fraction.

Discussion

As can be seen from the above experiments, the development of TH-expressing brain tumors in transgenic mice carrying SV40 T antigen directed by TH regulatory sequences demonstrates that the CNS catecholaminergic neurons are indeed susceptible to the effects of T antigen. This is in contrast to the results obtained with the glucagon enhancer directing expression of Tag to neurons in the brainstem (Efrat et al., supra). While Tag expression was detectable in specific brainstem neurons which are thought to be glucagon-expressing, no tumors arose. In the same animals, Tag could be seen in the appropriate cells of the endocrine pancreas as early as E10 when those cells are first detected (Pictet and Rutter, Handbook of Physiology, Section 7, eds., American Physiological Soc., 1972). At this site, the oncogene continued to be expressed throughout adulthood, leading to the formation of overt tumors by 9–12 months. Since Tag-expressing neurons in the CNS failed to proliferate, a possible implication was that CNS neurons were not susceptible to the effects of an oncogene. Recent experiments with the gonadotropin releasing hormone (GnRH) promoter driving SV40 T antigen have demonstrated that this is not the case for all neurons (Mellon et al., supra). Not only did the transgenic mice develop tumors but the neuronal cell lines isolated from such tumors continued to produce both GnRH and Tag. While it is likely that glucagon expression in the CNS is restricted to post-mitonic neurons, the GnRH-expressing hypothalamic neurons, which are thought to arise from the olfactory placode, have been shown to express the hormone while still dividing (Schwanzel-Fukuda and Pfaff, Nature, 338:161–163, 1989). These results might suggest that Tag needs to be expressed in a dividing cell in order to initiate transformation. This explanation is not entirely consistent with results using a PNMT-Tag transgene (Hammang et al., supra). Retinal tumors were observed in these transgenic mice in amacrine cells which are thought to be post-mitotic at the time when PNMT is first expressed. However, the cell-type of origin for the amacrine cell cultures derived from these tumors is unclear since these cells did not produce PNMT. They also did not express other catecholaminergic properties although the lack of TH and other catecholaminergic traits may be due to the fact that a significant percentage of PNMT-positive amacrine cells normally do not produce TH (Hadjiconstantinou et al., Neuroscience, 13:547–551, 1984; Park et al., J. Neurosc., 6:1108–1113, 1986). Nevertheless, the lack of PNMT in cultured cells was surprising and was suggested by the authors to be due to a repression of the differentiated phenotype by Tag. Therefore, the issue as to whether a post-mitotic neuron can be immortalized by the action of Tag remained unresolved in these experiments.

Our results clearly show that TH-producing CNS tumors can be obtained despite the fact that TH expression in the brain is observed only in post-mitotic neurons in vivo (Specht et al., supra). One possibility for the success of the TH promoter may be due to the fact that TH is an early marker of differentiated catecholaminergic neurons. In the rat CNS, TH is first detected in cells at E10.5, within one day of the birth of these cells (Foster et al., J. Comp. Neurol., 236:348–381, 1985). Thus, even though TH is expressed by post-mitotic neurons, the presence of Tag so early in development might allow the cell to re-enter the cell-cycle while maintaining differentiated properties. In contrast, expression of Tag late in development, with the glucagon or PNMT promoter constructs, may be incapable of driving a neuron back into the cell-cycle after it has been withdrawn from the cycle for a number of days. This differential susceptibility of a neuron to oncogenesis based on its developmental status could account for the lack of tumors in some tissues and their presence in others.

The observation that brain tumors only arose in adults and at various ages from 15 weeks to 8.5 months but were always present in the same location in the brain even though Tag itself was present in other regions implies two things. First, that Tag by itself is not sufficient to induce tumors in the brain and second, that some cells in the midbrain or brainstem are more likely than others to undergo complete transformation.

The observation that SV40 large T antigen requires additional transforming events in order to cause neoplasia is well established. The multi-step process hypothesized for tumorigenesis (Foulds, J. Chronic Dis., 8:2–37, 1958) has been strongly supported by experiments with primary cells in tissue culture (Land et al., Nature, 304:596–602, 1983; Yancopoulos et al., Proc. Natl. Acad. Sci. USA, 82:5455–5459, 1985) and with transgenic mice in vivo (Sinn et al., supra; Hanahan, 1985, supra; Mahon et al., Science, 235:1622–1628, 1987). The lack of brain tumors with the glucagon-Tag transgene (Efrat et al., supra) could be due to the smaller number of glucagon-positive cells as compared to the number of TH-positive cells. The smaller number of glucagon-positive cells would reduce the number of potential targets for subsequent 'hits' needed for full transformation.

The fact that TH-producing tumors always arose in the same location in the brain demonstrate that cells in this area are more prone to neoplasia. Possibly, Tag is expressed earlier in development in these susceptible cells. Alternatively, it may be that the TH-expressing cells of this region can transcribe Tag more efficiently because of the presence of appropriate trans-activating factors which would efficiently activate the TH promoter as compared to non-TH-expressing neurons in other brain regions. This difference in Tag levels might account for the relative ease with which transformation is accomplished in TH-expressing cells. Variations in the amount of the SV40 large T antigen protein are indeed present in different tissues and cells leading to a variable transforming capability by the oncogene (Small et al., Mol. Cell. Biol., 5:642–648, 1985). In this study, the SV40 DNA was injected into mice and Tag RNA could be detected at varying levels in different tissues. When injected into nude mice, cultured cells from all these tissues, except lung, were found to induce tumors in vivo. The inability of lung cells to generate tumors was correlated with the reduced levels of Tag mRNA in cultured lung cells.

The absence of Tag staining in some TH-expressing tissues such as the olfactory bulb (OB and sympathetic ganglia (SCG) is likely to reflect the lack of appropriate tissue-specific elements in 773 bp of TH upstream region. A similar pattern of Tag expression was found in transgenic mice in which 2.8 kb of 5' TH DNA was used. While these transgenic mice developed CNS tumors similar to the −773 TH-Tag mice, they also failed to express Tag in the OB and SCG. Recently, Kaneda et al. (1991), using the entire coding region of the human TH gene including 2.5 kb of 5' flanking DNA and 0.5 kb of 3' flanking DNA, demonstrated a strong expression in CNS regions like the striatum and hippocampus. Unfortunately, expression in the OB and SCG was not reported in these studies. In contrast, a longer 5' flanking region (4.8 kb) of the rat TH gene appears to contain all the elements for correct tissue-specific expression in transgenic mice (Example 1, supra). Creation of transgenic mice bearing the 4.8 kb TH-Tag construct was in fact attempted but only 1/47 pups carried the transgene and that one lineage was non-expressing, suggesting that the transgene may have had a deleterious effect during development.

Several lines of evidence demonstrate that CATH.a, PATH.1 and PATH.2 are noradrenergic. They synthesize active forms of the enzymes TH and DBH and produce the catecholamines DA and NE. The activities of the two enzymes are similar to those in the PC12 cell line. The activity of TH in PC12 cells, as initially reported, was 39± pmol/min/mg protein (Greene and Tischler, supra) which is 6–30 fold less than in the TH-Tag lines. However, TH activity has been shown to be subject to changes in plating density, media and/or serum (Lucas et al., Exp. Cell Res., 121:79–86, 1979; Tank et al., supra). DBH, on the other hand, has an activity level of 806±84 pmol/min/mg protein in PC12 cells, which is approximately 5–7 fold more than in the TH-Tag lines. The levels of DA and NE in PC12 cells are 16.6±1.7 and 6.1±6 nmol/mg protein respectively, which are much higher than in the TH-Tag lines. This may be because of the TH-Tag lines secrete large amounts of catecholamines into the tissue culture medium.

The presence of neurofilaments, the intermediate filaments in neurons and the absence of glial acidic protein, characteristic of glial cells, implies that the TH-Tag cell lines are neuronal in origin. The presence of synaptophysin or p38 in the TH-Tag cell lines suggests the existence of synaptic vesicles, although the presence of vesicles needs to be confirmed by ultrastructural analysis. It is interesting that the apparent molecular weight of p38 in all three cell lines is higher than in the rat brain synaptosomal preparation. This may be due to different post-translational modifications in the transformed cells, since other neuro-endocrine tumors and neuroblastomas also exhibit these differences (Weidenmann and Huttner, Virchows Archiv. B Cell Pathol., 58:95–121, 1989).

Synaptophysin or p38 is an integral membrane protein with a molecular weight of 38 kD. It is inserted in the membranes of small vesicles found only in neurons and neuroendocrine cells (Navone et al., supra.). In neurons these vesicles have been shown to function as storage sites for non-peptidergic neurotransmitters and to participate in their regulated release via exocytosis. In endocrine cells the function of p38 containing vesicles is not well understood (Johnston et al., supra). The pattern of staining for synaptophysin in our cells is very similar to that in PC12 cells, where the majority of staining has been shown to be centered about the Golgi complex (Johnston et al., supra). If synaptophysin is incorporated into vesicles they may tend to pool near the Golgi complex, their site of synthesis. Since PATH and CATH.a lack neurites they may lack the machinery necessary to transport vesicles to the periphery and hence accumulate more vesicles over the Golgi complex.

The small cell size and the large nuclear to cytoplasmic ratio suggests that the three lines originated from relatively immature cells. The PATH lines are likely to have arisen from precursors in the chromaffin lineage in the adrenal medulla. The lack of E is consistent with the immortalization of a precursor cell, since immature sympathoadrenal cells tend to be noradrenergic. The noradrenergicphenotype of CATH.a is consistent with an origin in the NE neurons of the brainstem, mainly located in the locus coeruleus and lateral tegmental area. However a more rigorous biochemical and physiological examination is required before the origin can be fully established. It would be of interest to determine whether CATH.a bears receptors for GABA (Cedarbaum and Aghajanian, Brain Res., 112:413–419, 1976), 5-HT (Segal, J. Physiol., 286:401–415, 1979), opiates (Atweh and Kuhar, Brain Res., 129:1–12, 1977) and NE (Aghajanian et al., Brain Res., 136:570–577, 1977), as has been demonstrated for locus coeruleus neurons.

In conclusion, our results demonstrate that promoter directed oncogenesis in transgenic animals can be used to establish CNS cell lines from post-mitotic neurons. Since our cell lines retain high levels of catecholamine expression, they should be useful for a variety of studies involving gene regulation and transplantation and should serve as good sources for the isolation of tissue-specific transcription factors.

What is claimed is:

1. An immortalized catecholaminergic mouse central nervous system neuronal cell line, wherein the cell line is ATCC Accession No. CRL 11179.

2. An immortalized neuronal cell obtainable from, and having the identifying characteristics of, ATCC Accession No. CRL 11179.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 37 base pairs
( B ) TYPE: nucleic acid
( C ) STRANDEDNESS: unknown
( D ) TOPOLOGY: unknown ( x i ) SEQUENCE DESCRIPTION: SEQ ID NO:1:

CGCCTGCCTG GCGAGGGCTG TGGAGACACC CGGGTGG 37

( 2 ) INFORMATION FOR SEQ ID NO:2:

( i ) SEQUENCE CHARACTERISTICS:
( A ) LENGTH: 96 base pairs
( B ) TYPE: nucleic acid
( C ) STRANDEDNESS: unknown
( D ) TOPOLOGY: unknown ( x i ) SEQUENCE DESCRIPTION: SEQ ID NO:2:

CGCCTGCCTG GCGAGGGCTG TGGAGACACC CGGGTGGCGA GTCGACGGCG CCTGCCTGGC 60

GAGGGCTGTG GAGACACCCG GGTGGCGAGT CGACGG 96